(12) United States Patent
Kim et al.

(10) Patent No.: US 11,008,343 B2
(45) Date of Patent: May 18, 2021

(54) HETEROCYCLIC COMPOUND AND ORGANIC ELECTRONIC DEVICE COMPRISING SAME

(71) Applicant: LG CHEM, LTD., Seoul (KR)

(72) Inventors: Ji Hoon Kim, Daejeon (KR); Jiyoung Lee, Daejeon (KR); Songrim Jang, Daejeon (KR); Doowhan Choi, Daejeon (KR); Bogyu Lim, Daejeon (KR); Junghyun Park, Daejeon (KR)

(73) Assignee: LG CHEM, LTD.

( * ) Notice: Subject to any disclaimer, the term of this patent is extended or adjusted under 35 U.S.C. 154(b) by 374 days.

(21) Appl. No.: 16/318,277

(22) PCT Filed: Jan. 31, 2018

(86) PCT No.: PCT/KR2018/001325
§ 371 (c)(1),
(2) Date: Jan. 16, 2019

(87) PCT Pub. No.: WO2018/216880
PCT Pub. Date: Nov. 29, 2018

(65) Prior Publication Data
US 2019/0284210 A1    Sep. 19, 2019

(30) Foreign Application Priority Data

May 24, 2017  (KR) .......................... 10-2017-0064097
Oct. 13, 2017  (KR) .......................... 10-2017-0133228

(51) Int. Cl.
*H01L 51/50* (2006.01)
*C07D 519/00* (2006.01)
(Continued)

(52) U.S. Cl.
CPC ......... *C07D 519/00* (2013.01); *C07D 495/04* (2013.01); *H01L 51/0036* (2013.01); *H01L 51/0052* (2013.01); *H01L 51/0068* (2013.01); *H01L 51/0071* (2013.01); *H01L 51/0072* (2013.01); *H01L 51/0074* (2013.01);
(Continued)

(58) Field of Classification Search
None
See application file for complete search history.

(56) References Cited

U.S. PATENT DOCUMENTS 5,331,183 A    7/1994  Sariciftci et al.
5,454,880 A    10/1995 Sariciftci et al.
(Continued)

FOREIGN PATENT DOCUMENTS

CN    104557968    4/2015
EP    2903047      8/2015
(Continued)

OTHER PUBLICATIONS

Yao et al. "Achieving Highly Efficient Nonfullerene Organic Solar Cells with Improved Intermolecular Interaction and Open-Circuit Voltage" Advanced Materials 29:1700254 (2017).
(Continued)

*Primary Examiner* — Gregory D Clark
(74) *Attorney, Agent, or Firm* — Myers Bigel, P.A.

(57) ABSTRACT

The present specification relates to a heterocyclic compound of Chemical Formula 1 and an organic electronic device including the same.

15 Claims, 3 Drawing Sheets

(51) Int. Cl.
  *H01L 51/00* (2006.01)
  *H01L 51/42* (2006.01)
  *C07D 495/04* (2006.01)

(52) U.S. Cl.
  CPC ........ *H01L 51/424* (2013.01); *H01L 51/4253* (2013.01); *H01L 51/4233* (2013.01); *Y02E 10/549* (2013.01)

(56) References Cited

U.S. PATENT DOCUMENTS

| | | | |
|---|---|---|---|
| 8,695,986 B2 | 4/2014 | Clemons et al. | |
| 2016/0351342 A1 | 12/2016 | Zakeeruddin et al. | |
| 2018/0057515 A1 | 3/2018 | Lim et al. | |
| 2020/0251661 A1* | 8/2020 | Kim | C07D 495/22 |

FOREIGN PATENT DOCUMENTS

| | | |
|---|---|---|
| JP | 5869480 | 2/2016 |
| KR | 101407138 | 8/2012 |
| KR | 1020150027344 | 3/2015 |
| KR | 1020160124705 | 10/2016 |
| KR | 101769665 | 8/2017 |

OTHER PUBLICATIONS

Cui et al. "Fine-Tuned Photoactive and Interconnection Layers for Achieving over 13% Efficiency in a Fullerene-Free Tandem Organic Solar Cell" Journal of the American Chemical Society 139:7302-7309 (2017).

Yu et al. "Polymer Photovoltaic Cells: Enhanced Efficiencies via a Network of Internal Donor-Acceptor Heterojunctions" Science 270:1789-1791 (1995).

Yang et al. "Halogenated conjugated molecules for ambipolar field-effect transistors and non-fullerene organic solar cells" Materials Chemistry Frontiers 1:1389-1395 (2017).

Yao et al. "Design and Synthesis of Low Bandgap Small Molecule Acceptor for Efficient Polymer Solar Cells" Advanced Materials 28:8283-8287 (2016).

International Search Report with English Language Translation of the International Searching Authority corresponding to International Patent Application No. PCT/KR2018/001325, dated May 11, 2018. (5 pages).

* cited by examiner

[Figure 1]
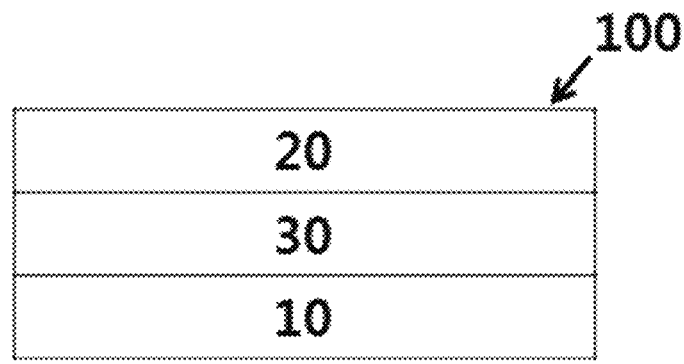
[Figure 2]
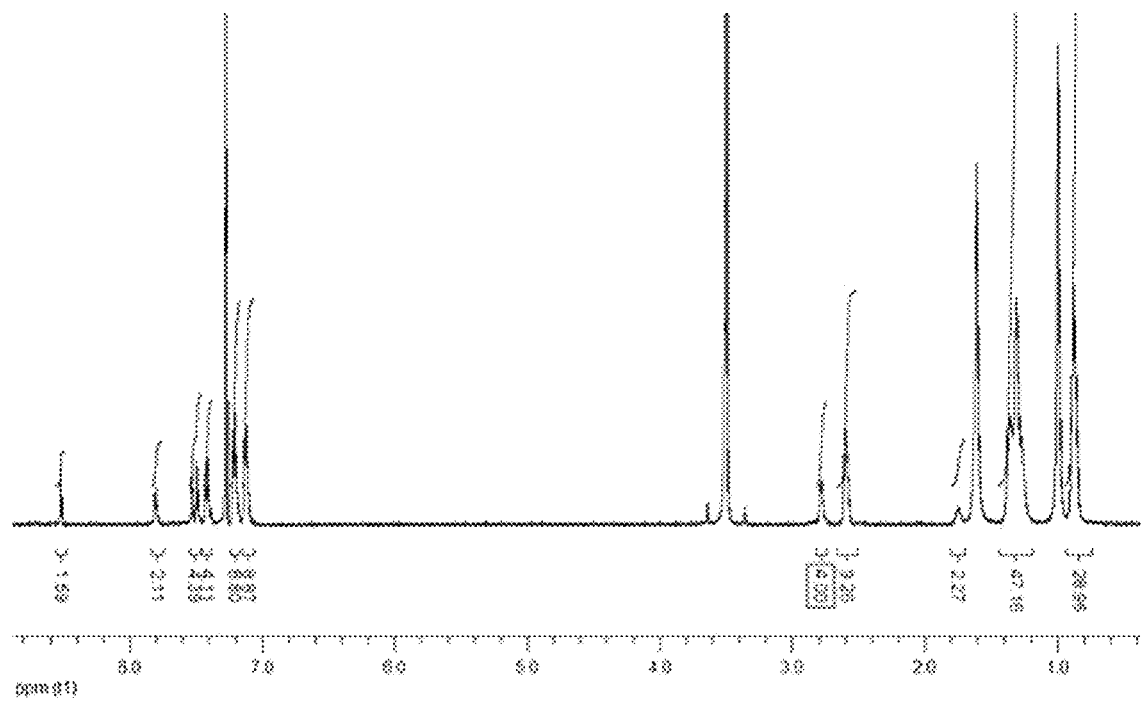

[Figure 3]
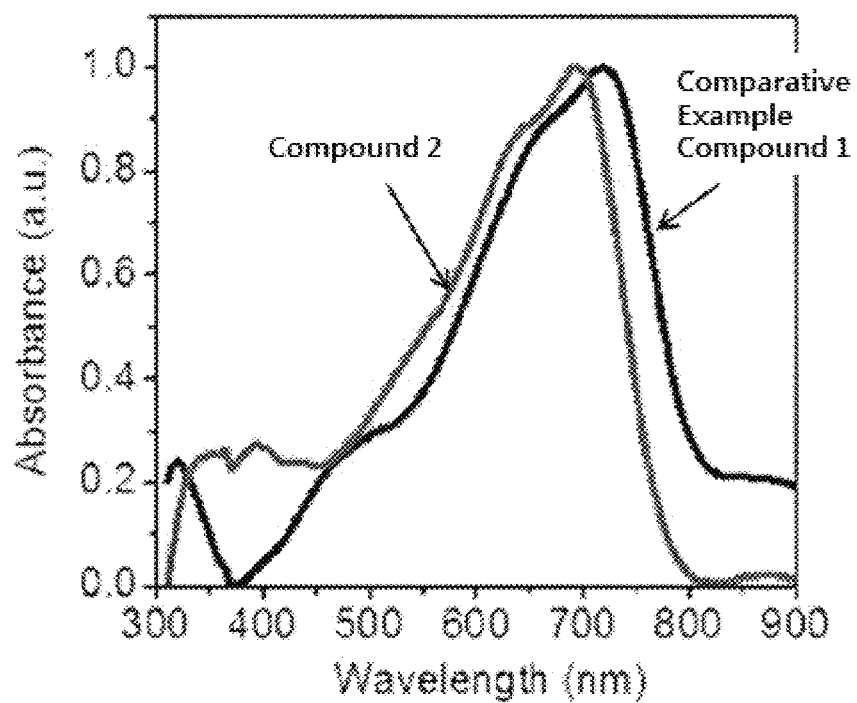

[Figure 4]
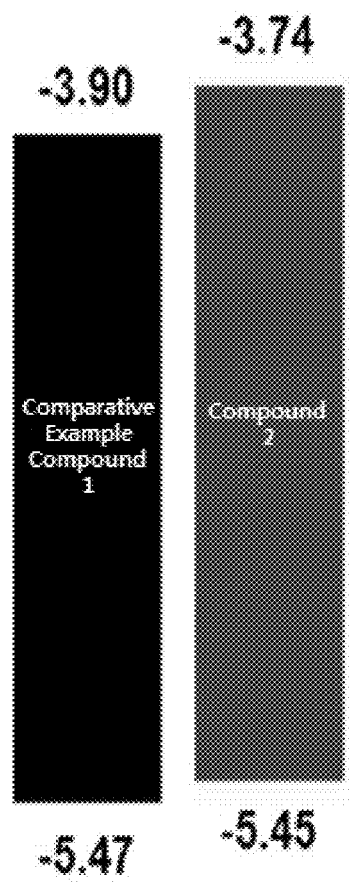

HETEROCYCLIC COMPOUND AND ORGANIC ELECTRONIC DEVICE COMPRISING SAME

CROSS REFERENCE TO RELATED APPLICATIONS

This application is a 35 U.S.C. § 371 national stage application of PCT International Application No. PCT/KR2018/001325, filed on Jan. 31, 2018, which claims priority from Korean Patent Application Nos. 10-2017-0064097 filed on May 24, 2017, and 10-2017-0133228 filed on Oct. 13, 2017, the contents of which are incorporated herein by reference in their entireties. The above reference PCT International Application was published in the Korean language as International Publication No. WO 2018/216880 A1 on Nov. 29, 2018.

TECHNICAL FIELD

The present specification relates to a heterocyclic compound and an organic electronic device including the same.

BACKGROUND ART

An organic electronic device means a device that requires an exchange of electric charges between electrodes using holes and/or electrons and organic materials. The organic electronic device may be largely divided into the following two categories depending on the operation principle. First, the organic electronic device is an electronic device in which an exciton is formed in an organic material layer by a photon that flows from an external light source to the device, the exciton is separated into electrons and holes, and the electrons and the holes are each transferred to different electrodes and used as an electric current source (voltage source). Second, the organic electronic device is an electronic device in which holes and/or electrons are injected into an organic material semiconductor that forms an interface with two or more electrodes by applying voltage or an electric current to the electrodes, and the device is operated by the injected electrons and holes.

Examples of an organic electronic device include an organic solar cell, an organic photoelectric device, an organic light emitting device, an organic transistor, and the like, and hereinafter, the organic photoelectric device will be mainly described in detail, but in the organic electronic devices, a hole injection or transporting material, an electron injection or transporting material, or a light emitting material is operated under similar principles.

For the organic solar cell, it is important to increase efficiency so as to output as much electric energy as possible from solar energy. In order to increase the efficiency of the organic solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases, and accordingly, manufacturing costs may be increased.

The organic photoelectric device is a device that converts light into electric signals by using the photoelectric effect, includes a photodiode, a phototransistor, and the like, and may be applied to an image sensor, and the like. In an image sensor including a photodiode, the resolution is increasing as the days go by, and accordingly, the pixel size is decreasing. Currently, in the case of a silicon photodiode mainly used, as the size of pixel is decreased, the absorption area is reduced, so that the reduction in sensitivity may occur.

Accordingly, organic materials capable of replacing silicon have been studied.

Since organic materials have a high extinction coefficient and may selectively absorb light in a specific wavelength region according to the molecular structure, the organic materials may replace a photodiode and a color filter, and thus, are very advantageous in improving sensitivity and high integration.

DISCLOSURE

Technical Problem

The present specification provides a heterocyclic compound and an organic electronic device including the same.

Technical Solution

An exemplary embodiment of the present specification provides a heterocyclic compound represented by the following Chemical Formula 1.

[Chemical Formula 1]

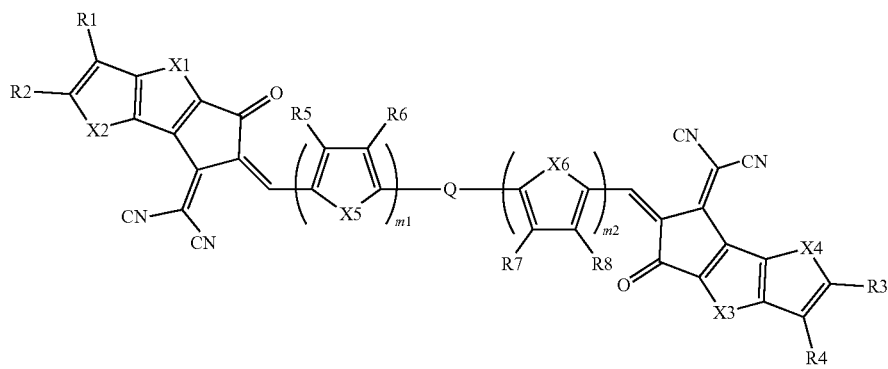

In Chemical Formula 1,

X1 to X6 are the same as or different from each other, and are each independently CRR', NR, O, SiRR', PR, S, GeRR', Se, or Te, R1 to R8, R, and R' are the same as or different from each other, and are each independently hydrogen; deuterium; a halogen group; a hydroxy group; a substituted or unsubstituted alkyl group; or a substituted or unsubstituted alkoxy group, m1 and m2 are each 0 or 1, Q is a structure represented by any one of the following Chemical Formulae A to C,

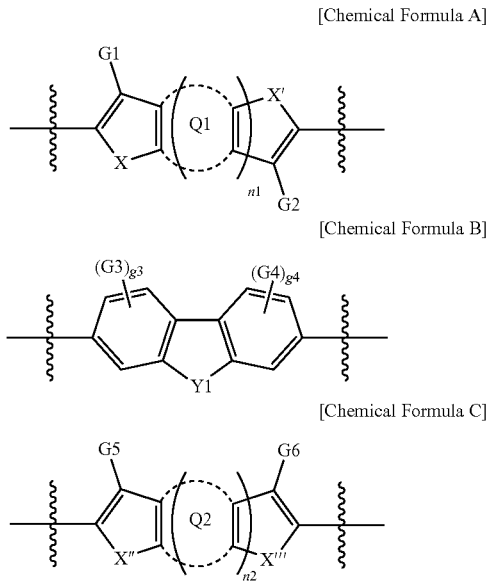

in Chemical Formulae A to C,

X, X', X", and X'" are the same as or different from each other, and are each independently S or Se, Y1 is CR"R'" or NR", G1 to G6, R", and R'" are the same as or different from each other, and are each independently hydrogen; deuterium; a halogen group; a hydroxy group; a substituted or unsubstituted alkyl group; a substituted or unsubstituted alkoxy group; a substituted or unsubstituted aryl group; or a substituted or unsubstituted heteroaryl group, Q1 and Q2 are the same as or different from each other, and are each independently a substituted or unsubstituted ring, g3 and g4 are each an integer of 1 to 3, n1 and n2 are each an integer of 1 to 5, when g3, g4, n1, and n2 are each 2 or more, two or more structures in the parenthesis are the same as or different from each other, and

is a moiety bonded to Chemical Formula 1.

Further, an exemplary embodiment of the present specification provides an organic electronic device including: a first electrode; a second electrode disposed to face the first electrode; and an organic material layer having one or more layers disposed between the first electrode and the second electrode, in which one or more layers of the organic material layer include the above-described heterocyclic compound.

Advantageous Effects

The heterocyclic compound represented by Chemical Formula 1 according to an exemplary embodiment of the present specification freely adjusts an energy absorption region and an energy level through various structures of dicyanomethylene-cyclopentathienothiophene-one which is an end in the molecule thereof, and Q which is a core in the molecule thereof, and an organic solar cell including the same has an excellent device performance.

Further, an organic solar cell in which the heterocyclic compound represented by Chemical Formula 1 is used as an n-type organic material layer of a photoactive layer exhibits excellent photoelectric conversion efficiency.

The heterocyclic compound represented by Chemical Formula 1 according to an exemplary embodiment of the present specification has a lowest unoccupied molecular orbital (LUMO) energy level similar to that of phenyl-C61-butyric acid methyl ester (PCBM) which is an existing fullerene-based acceptor material, but an organic solar cell in which the heterocyclic compound represented by Chemical Formula 1 is used as an n-type organic material layer of a photoactive layer exhibits high open-circuit voltage ($V_{oc}$) due to low loss of the open-circuit voltage.

Further, the heterocyclic compound represented by Chemical Formula 1 may exhibit better electron mobility by increasing molecule-molecule attraction through introduction of dicyanomethylene-cyclopentathienothiophene-one into the end, and accordingly, it is possible to manufacture an organic solar cell advantageous for a roll-to-roll process, that is, an organic solar cell capable of exhibiting an excellent performance even in a thin film having a large thickness.

The heterocyclic compound represented by Chemical Formula 1 according to an exemplary embodiment of the present specification may improve electron mobility by increasing molecule-molecule interaction through introduction of a dicyanomethylene-cyclopentathienothiophene-one end group which is an end in the molecule, may manufacture an organic photoelectric device having absorption regions in visible light and near infra red (NIR) regions by alleviating a solubility issue and inducing O—S interaction when an alkoxy group is introduced as a spacer into R5 to R8 of Chemical Formula 1, and is advantageous for a solution process during the manufacture of an organic photoelectric device by improving the solubility issue.

DESCRIPTION OF DRAWINGS

FIG. 1 is a view illustrating an organic electronic device according to an exemplary embodiment of the present specification.

FIG. 2 is a view illustrating a 1H-NMR spectrum of Compound 2 according to an exemplary embodiment of the present specification.

FIG. 3 is a view illustrating UV-vis absorption spectra in a film state with respect to Compound 2 according to an exemplary embodiment of the present specification and IEIC which is Comparative Example Compound 1.

FIG. 4 is a view illustrating HOMO/LUMO energy levels of Compound 2 according to an exemplary embodiment of the present specification and IEIC which is Comparative Example Compound 1.

EXPLANATION OF REFERENCE NUMERALS
AND SYMBOLS

100: Organic electronic device
10: First electrode
20: Second electrode
30: Photoactive layer

MODE FOR INVENTION

Hereinafter, the present specification will be described in detail.

The present specification provides the heterocyclic compound represented by Chemical Formula 1.

The heterocyclic compound represented by Chemical Formula 1 according to an exemplary embodiment of the present specification freely adjusts an energy absorption region and an energy level through various structures of dicyanomethylene-cyclopentathienothiophene-one which is an end in the molecule thereof, and Q which is a core in the molecule thereof, and an organic solar cell including the same has an excellent device performance.

Further, an organic solar cell in which the heterocyclic compound represented by Chemical Formula 1 is used as an n-type organic material layer of a photoactive layer exhibits excellent photoelectric conversion efficiency.

The heterocyclic compound represented by Chemical Formula 1 according to an exemplary embodiment of the present specification has a LUMO energy level similar to that of PCBM which is an existing fullerene-based acceptor material, but an organic solar cell in which the heterocyclic compound represented by Chemical Formula 1 is used as an n-type organic material layer (electron acceptor material) of a photoactive layer exhibits high open-circuit voltage ($V_{oc}$) due to low loss of the open-circuit voltage.

Further, the heterocyclic compound represented by Chemical Formula 1 according to an exemplary embodiment of the present specification may improve electron mobility by increasing molecule-molecule interaction through introduction of dicyanomethylene-cyclopentathienothiophene-one which is an end in the molecule, may manufacture an organic photoelectric device having absorption regions in visible light and near infra red (NIR) regions by alleviating a solubility issue and inducing O—S interaction when an alkoxy group is introduced as a spacer into R5 to R8 of Chemical Formula 1, and is advantageous for a solution process during the manufacture of an organic photoelectric device by improving the solubility issue.

When one part "includes" one constituent element in the present specification, unless otherwise specifically described, this does not mean that another constituent element is excluded, but means that another constituent element may be further included.

When one member is disposed "on" another member in the present specification, this includes not only a case where the one member is brought into contact with another member, but also a case where still another member is present between the two members.

Examples of the substituents will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or more substituents selected from the group consisting of deuterium; a halogen group; an alkyl group; an alkenyl group; an alkoxy group; a thioalkoxy group; an ester group; a carbonyl group; a carboxyl group; a hydroxy group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heteroarylamine group; an arylamine group; an aryl group; a nitrile group; a nitro group; a hydroxy group; and a heterocyclic group including one or more of N, O, and S atoms, or having no substituent.

The substituents may be unsubstituted or substituted with an additional substituent.

In the present specification, a halogen group may be fluorine, chlorine, bromine, or iodine.

In the present specification, the number of carbon atoms of an imide group is not particularly limited, but is preferably 1 to 25. Specifically, the imide group may be a compound having the following structures, but is not limited thereto.

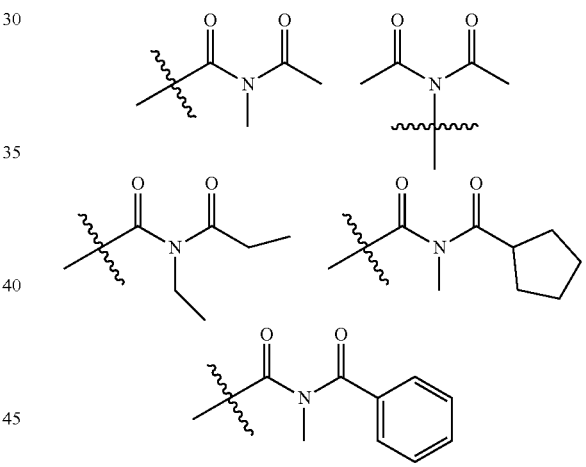

In the present specification, for an amide group, one or two nitrogen atoms of the amide group may be substituted with hydrogen, a straight, branched, or cyclic alkyl group having 1 to 25 carbon atoms, or an aryl group having 6 to 25 carbon atoms. Specifically, the amide group may be a compound having the following structural formulae, but is not limited thereto.

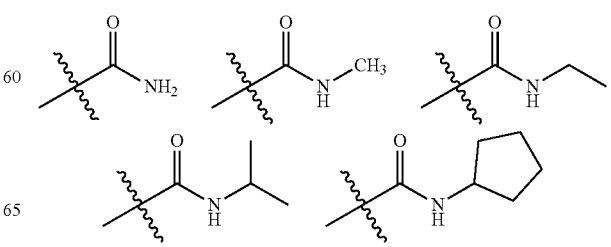

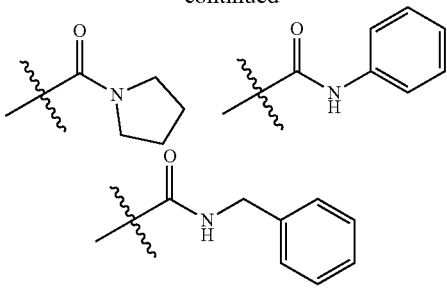

In the present specification, the alkyl group may be straight or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight, branched, or cyclic. The number of carbon atoms of the alkoxy group is not particularly limited, but is preferably 1 to 20. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the description on the alkoxy group may be applied to the thioalkoxy group, except that O of the alkoxy group is S.

In the present specification, the alkenyl group may be straight or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —BR$_{100}$R$_{101}$, and R$_{100}$ and R$_{101}$ are the same as or different from each other, and may be each independently selected from the group consisting of hydrogen; deuterium; halogen; a nitrile group; a substituted or unsubstituted monocyclic or polycyclic cycloalkyl group having 3 to 30 carbon atoms; a substituted or unsubstituted straight or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, a dinaphthylphosphine oxide group, and the like, but are not limited thereto.

In the present specification, an aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group has a structure in which two cyclic organic compounds are linked to each other through one atom.

In the present specification, the fluorenyl group may be substituted, and adjacent substituents may be bonded to each other to form a ring.

When the fluorenyl group is substituted, the fluorenyl group may be

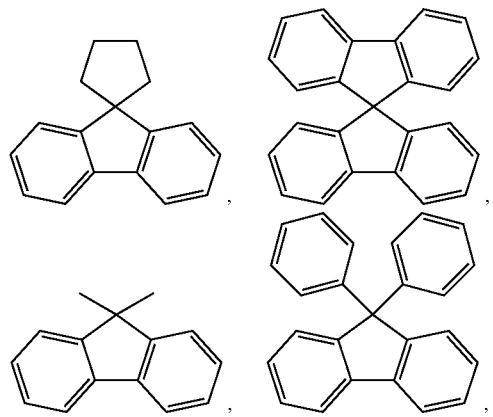

and the like. However, the fluorenyl group is not limited thereto.

In the present specification, a heteroaryl group is a heteroaryl group including one or more of O, N, and S as a hetero element, and the number of carbon atoms thereof is not particularly limited, but is preferably 2 to 60. Examples of the heteroaryl group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a benzothiadiazolyl group, a phenothiazinyl group, a dibenzofuranyl group, and the like, but are not limited thereto.

In the present specification, a heterocyclic group may be monocyclic or polycyclic, may be an aromatic ring, an aliphatic ring, or a fused ring of the aromatic ring and the aliphatic ring, and may be selected from the examples of the heteroaryl group.

In the present specification, examples of an arylamine group include a substituted or unsubstituted monoarylamine group or a substituted or unsubstituted diarylamine group. The aryl group in the arylamine group may be a monocyclic aryl group or a polycyclic aryl group. The arylamine group including two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, the heteroaryl group in the heteroarylamine group may be selected from the above-described examples of the heterocyclic group.

In the present specification, the aryl group in the aryloxy group, the arylthioxy group, the arylsulfoxy group, and the aralkylamine group is the same as the above-described examples of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, the alkyl group in the alkylthioxy group and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include a methylsulfoxy group, an ethylsulfoxy group, a propylsulfoxy group, a butylsulfoxy group, and the like, but the examples are not limited thereto.

In the present specification, in a substituted or unsubstituted ring formed by bonding adjacent groups, the "ring" means a substituted or unsubstituted hydrocarbon ring; or a substituted or unsubstituted hetero ring.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more atoms other than carbon, that is, one or more heteroatoms, and specifically, the heteroatom may include one or more atoms selected from the group consisting of O, N, Se, S, and the like. The hetero ring may be monocyclic or polycyclic, may be an aromatic ring, an aliphatic ring, or a fused ring of the aromatic ring and the aliphatic ring, and may be selected from the examples of the heteroaryl group or the heterocyclic group, except for the hetero ring which is not monovalent.

According to an exemplary embodiment of the present specification, Q1 and Q2 are the same as or different from each other, and are each independently a substituted or unsubstituted aromatic ring; or a substituted or unsubstituted hetero ring.

According to an exemplary embodiment of the present specification, Chemical Formula 1 is represented by any one of the following Chemical Formulae 1-1 to 1-3.

[Chemical Formula 1-1]

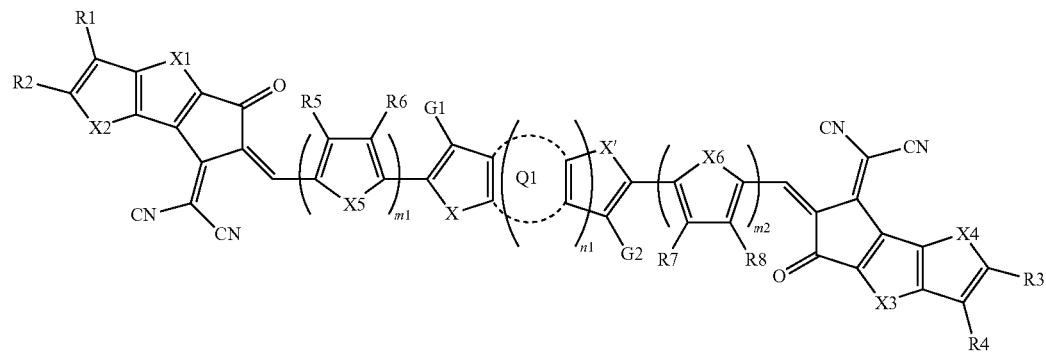

[Chemical Formula 1-2]

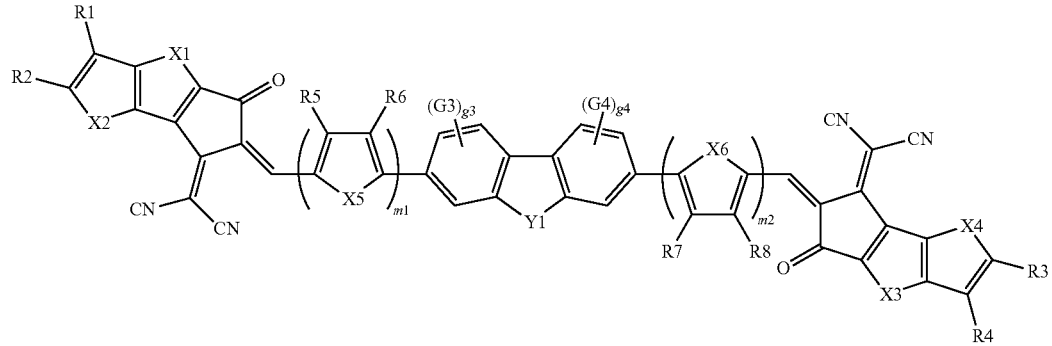

[Chemical Formula 1-3]

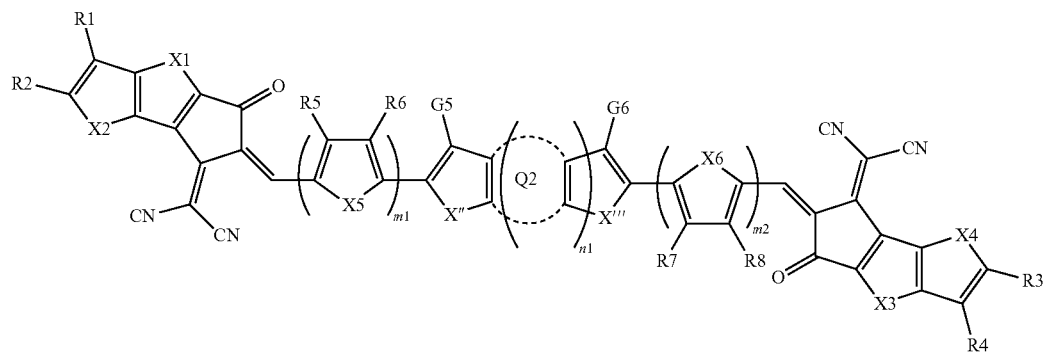

In Chemical Formulae 1-1 to 1-3, definitions of X1 to X4, R1 to R8, m1, and m2 are the same as those defined in Chemical Formula 1, definitions of Q1, X, X', n1, G1, and G2 are the same as those defined in Chemical Formula A, definitions of Y1, G3, G4, g3, and g4 are the same as those defined in Chemical Formula B, and definitions of Q2, X", X'", n2, G5, and G6 are the same as those defined in Chemical Formula C.

According to an exemplary embodiment of the present specification, in Chemical Formula A, n1 is an integer of 2 to 5.

According to an exemplary embodiment of the present specification, Chemical Formula A is selected from the following structures.

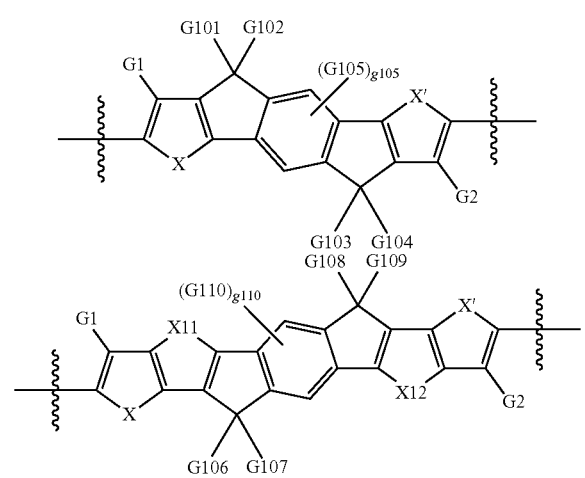

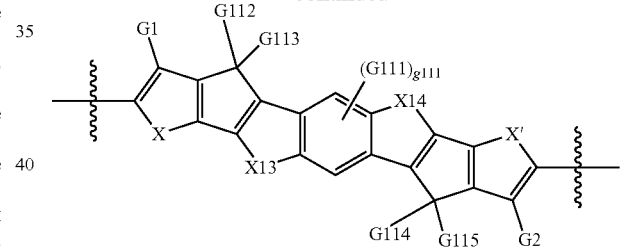

In the structures, definitions of X, X', G1, and G2 are the same as those defined in Chemical Formula A, X11 to X14 are the same as or different from each other, and are each independently S or Se, G101 to G115 are the same as or different from each other, and are each independently hydrogen; deuterium; a halogen group; a hydroxy group; a substituted or unsubstituted alkyl group; a substituted or unsubstituted alkoxy group; a substituted or unsubstituted aryl group; or a substituted or unsubstituted heteroaryl group, g105, g110, and g111 are each 1 or 2, and when g105, g110, and g111 are each 2, two structures in the parenthesis are the same as or different from each other.

According to an exemplary embodiment of the present specification, Chemical Formula B is selected from the following structures.

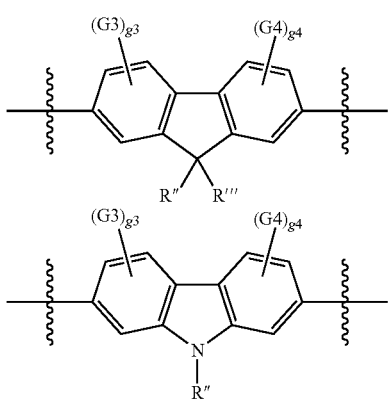

In the structures, definitions of G3, G4, g3, and g4 are the same as those defined in Chemical Formula B, and R″ and R‴ are the same as or different from each other, and are each independently hydrogen; deuterium; a halogen group; a hydroxy group; a substituted or unsubstituted alkyl group; a substituted or unsubstituted alkoxy group; a substituted or unsubstituted aryl group; or a substituted or unsubstituted heteroaryl group.

According to an exemplary embodiment of the present specification, in Chemical Formula C, n2 is an integer of 2 to 5.

According to an exemplary embodiment of the present specification, Chemical Formula C is represented by the following structure.

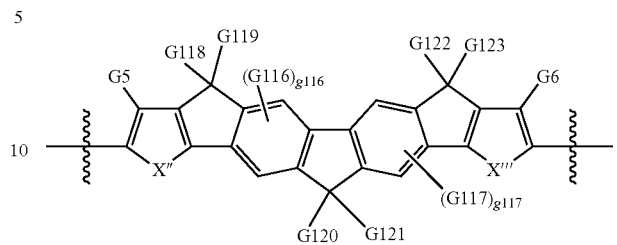

In the structure, definitions of X″, X‴, G5, and G6 are the same as those defined in Chemical Formula C, G116 to G123 are the same as or different from each other, and are each independently hydrogen; deuterium; a halogen group; a hydroxy group; a substituted or unsubstituted alkyl group; a substituted or unsubstituted alkoxy group; a substituted or unsubstituted aryl group; or a substituted or unsubstituted heteroaryl group, g116 and g117 are each 1 or 2, and when g116 and g117 are each 2, two structures in the parenthesis are the same as or different from each other.

According to an exemplary embodiment of the present specification, Chemical Formula 1 is represented by any one of the following Chemical Formulae 1-4 to 1-15.

[Chemical Formula 1-4]

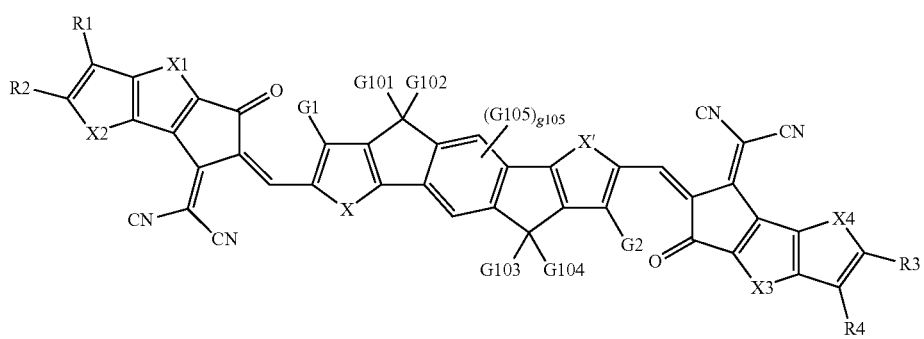

[Chemical Formula 1-5]

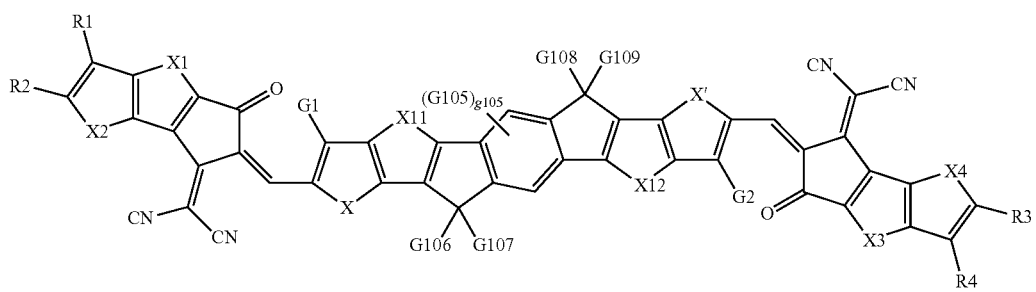

[Chemical Formula 1-6]
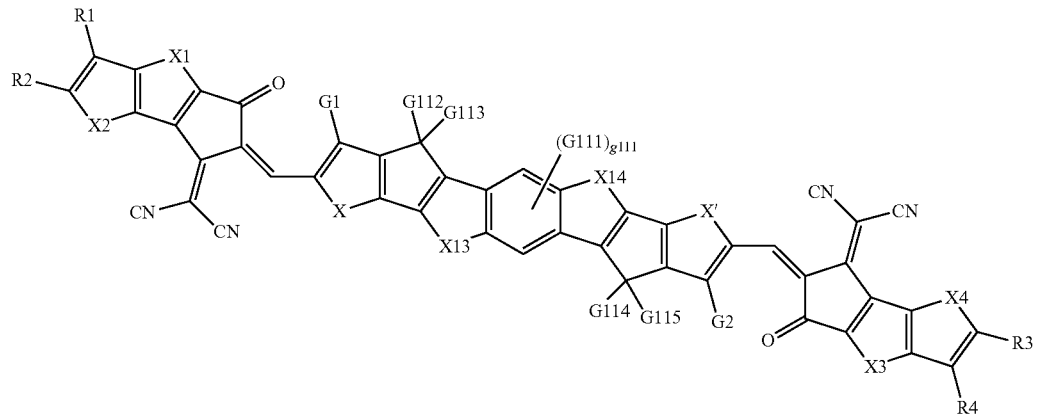
[Chemical Formula 1-7]
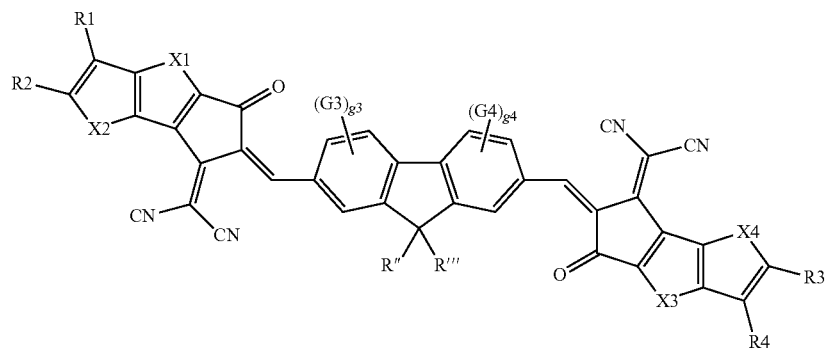
[Chemical Formula 1-8]
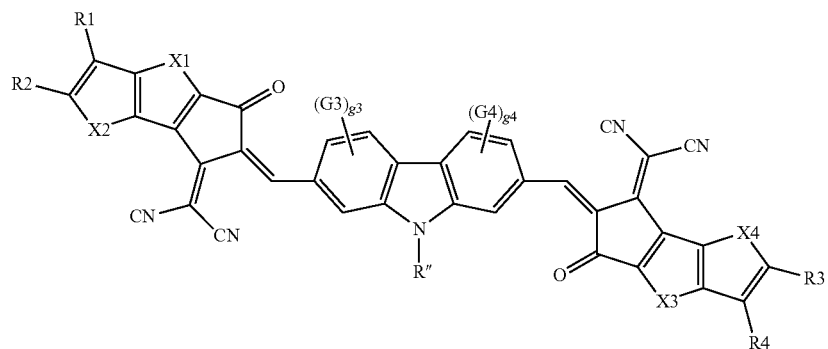
[Chemical Formula 1-9]
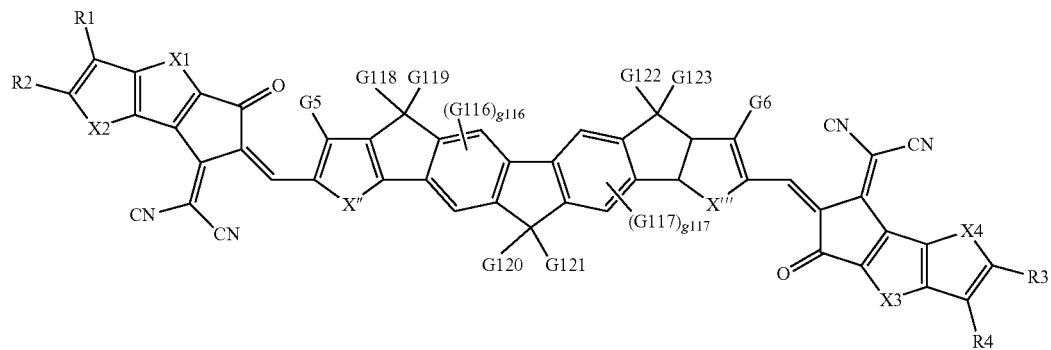

[Chemical Formula 1-10]
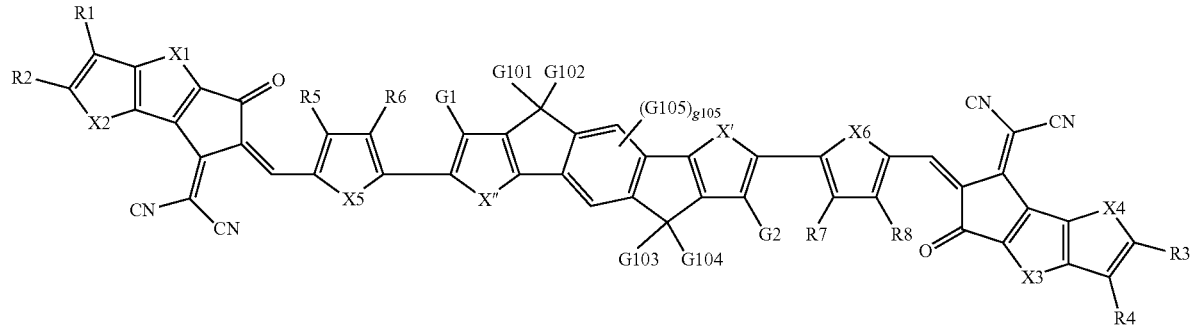
[Chemical Formula 1-11]
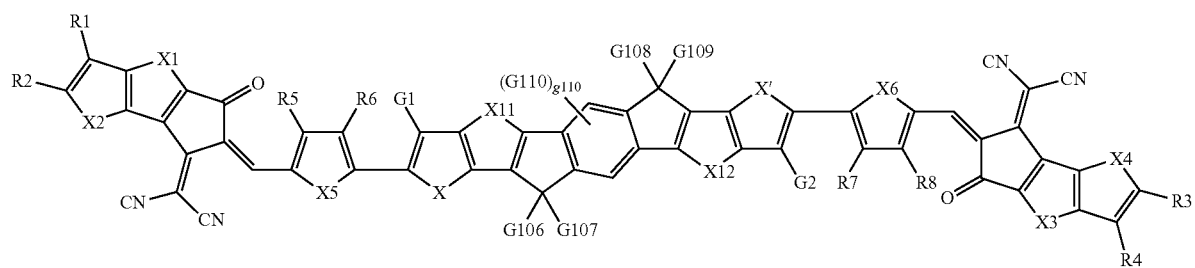
[Chemical Formula 1-12]
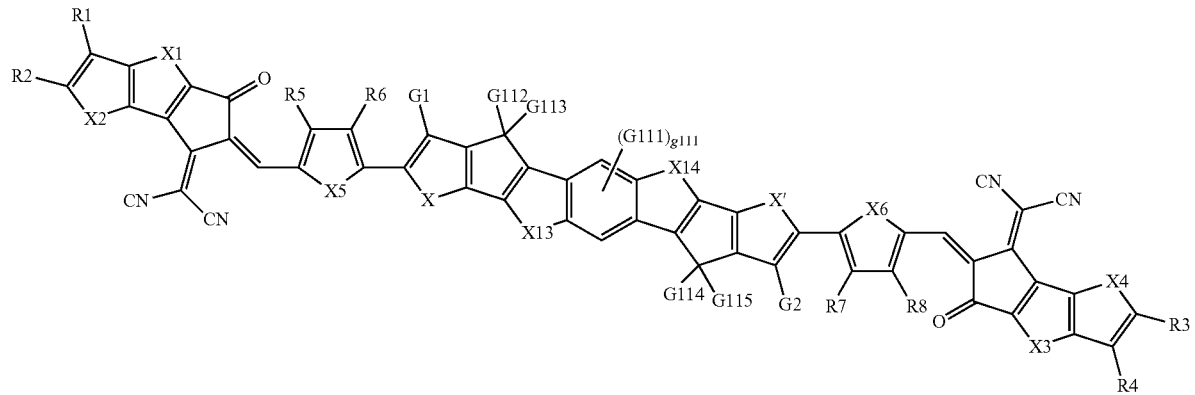
[Chemical Formula 1-13]
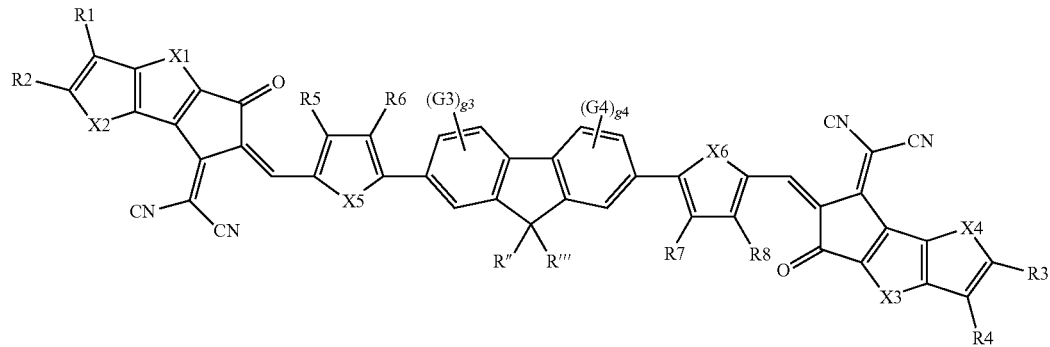

[Chemical Formula 1-14]

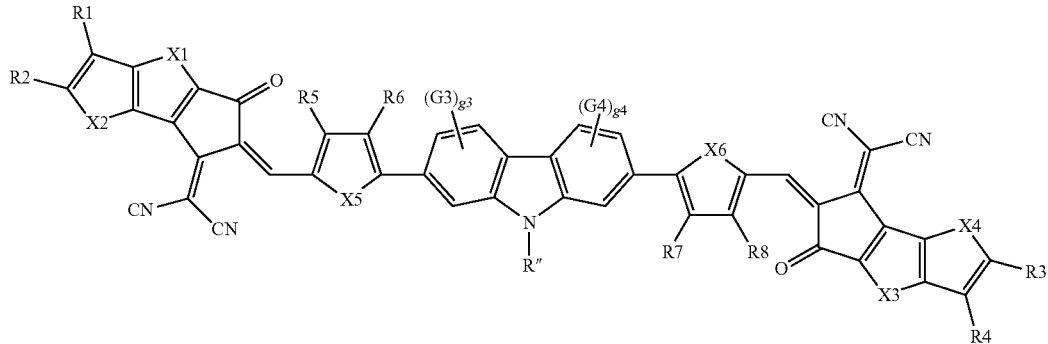

[Chemical Formula 1-15]

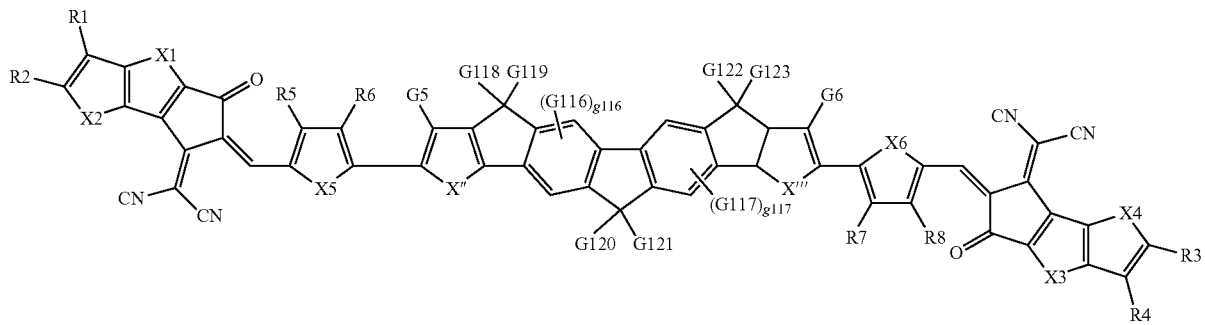

In Chemical Formulae 1-4 to 1-15, definitions of X1 to X4 and R1 to R8 are the same as those defined in Chemical Formula 1, definitions of X, X', G1, and G2 are the same as those defined in Chemical Formula A, definitions of G3, G4, g3, and g4 are the same as those defined in Chemical Formula B, definitions of X", X'", G5, and G6 are the same as those defined in Chemical Formula C, X11 to X14 are the same as or different from each other, and are each independently S or Se, G101 to G123, R", and R'" are the same as or different from each other, and are each independently hydrogen; deuterium; a halogen group; a hydroxy group; a substituted or unsubstituted alkyl group; a substituted or unsubstituted alkoxy group; a substituted or unsubstituted aryl group; or a substituted or unsubstituted heteroaryl group, g105, g110, g111, g116, and g117 are each 1 or 2, and when g105, g110, g111, g116, and g117 are each 2, two structures in the parenthesis are the same as or different from each other.

According to an exemplary embodiment of the present specification, Q1 and Q2 are the same as or different from each other, and are each independently a substituted or unsubstituted benzene ring; a substituted or unsubstituted thiophene ring; a substituted or unsubstituted fluorene ring; a substituted or unsubstituted cyclopentadiene ring; or a substituted or unsubstituted indene ring.

According to an exemplary embodiment of the present specification, Q1 and Q2 are the same as or different from each other, and are each independently a benzene ring which is unsubstituted or substituted with a heteroaryl group substituted with one or more selected from the group consisting of a halogen group, an alkyl group, and a thioalkoxy group; a thiophene ring; a fluorene ring substituted with an alkyl group; a cyclopentadiene ring substituted with an alkyl group; an indene ring substituted with an alkyl group; a cyclopentadiene ring substituted with an aryl group substituted with an alkyl group; a cyclopentadiene ring substituted with a heteroaryl group substituted with an alkyl group; an indene ring substituted with an aryl group substituted with an alkyl group; or an indene ring substituted with a heteroaryl group substituted with an alkyl group.

According to an exemplary embodiment of the present specification, Q1 and Q2 are the same as or different from each other, and are each independently a benzene ring; a benzene ring substituted with a thiophene group substituted with fluorine and a 2-ethylhexyl group; a benzene ring substituted with a thiophene group substituted with a 2-ethylhexyl group; a benzene ring substituted with a thiophene group substituted with a 2-ethylhexylthioxy group; a thiophene ring; a fluorene ring substituted with an n-octyl group; a cyclopentadiene ring substituted with an n-octyl group; an indene ring substituted with an n-octyl group; a cyclopentadiene ring substituted with a phenyl group substituted with an n-hexyl group; a cyclopentadiene ring substituted with a thiophene group substituted with an n-hexyl group; an indene ring substituted with a phenyl group substituted with an n-hexyl group; or an indene ring substituted with a thiophene group substituted with an n-hexyl group.

According to an exemplary embodiment of the present specification, X1 to X4, X, X', X", X'", and X11 to X14 are S.

According to an exemplary embodiment of the present specification, R5 to R8 are the same as or different from each other, and are each independently hydrogen; a substituted or unsubstituted alkyl group; or a substituted or unsubstituted alkoxy group.

According to an exemplary embodiment of the present specification, R1 to R5, R8, G1, G2, G5, and G6 are hydrogen.

According to an exemplary embodiment of the present specification, R6 and R7 are the same as or different from each other, and are each independently a substituted or unsubstituted alkyl group; or a substituted or unsubstituted alkoxy group.

According to an exemplary embodiment of the present specification, R6 and R7 are the same as or different from each other, and are each independently an alkyl group; or an alkoxy group.

According to an exemplary embodiment of the present specification, R6 and R7 are the same as or different from each other, and are each independently a 2-ethylhexyl group; or a 2-ethylhexyloxy group.

According to an exemplary embodiment of the present specification, G105, G110, G116, and G117 are hydrogen.

According to an exemplary embodiment of the present specification, G101 to G104, G106 to G109, G111 to G115, G118, G119, G122, and G123 are the same as or different from each other, and are each independently a substituted or unsubstituted aryl group; or a substituted or unsubstituted heteroaryl group.

According to an exemplary embodiment of the present specification, G101 to G104, G106 to G109, G111 to G115, G118, G119, G122, and G123 are the same as or different from each other, and are each independently a substituted or unsubstituted phenyl group; or a substituted or unsubstituted thiophene group.

According to an exemplary embodiment of the present specification, G101 to G104, G106 to G109, G111 to G115, G118, G119, G122, and G123 are the same as or different from each other, and are each independently a phenyl group which is unsubstituted or substituted with an alkyl group; a thiophene group which is unsubstituted or substituted with an alkyl group or a thioalkoxy group; or a thiophene group which is unsubstituted or substituted with a halogen group and an alkyl group.

According to an exemplary embodiment of the present specification, G101 to G104, G106 to G109, G111 to G115, G118, G119, G122, and G123 are the same as or different from each other, and are each independently a phenyl group which is unsubstituted or substituted with an n-hexyl group; a phenyl group which is unsubstituted or substituted with a 2-ethylhexyl group; a thiophene group which is unsubstituted or substituted with an n-hexyl group; a thiophene group which is unsubstituted or substituted with a 2-ethylhexyl group; a thiophene group which is unsubstituted or substituted with a 2-ethylhexylthioxy group; or a thiophene group which is unsubstituted or substituted with fluorine and a 2-ethylhexyl group.

According to an exemplary embodiment of the present specification, G101 to G104, G106 to G109, G111 to G115, G118, G119, G122, and G123 are the same as or different from each other, and are each independently a phenyl group; a phenyl group substituted with an n-hexyl group; a phenyl group substituted with a 2-ethylhexyl group; a thiophene group; a thiophene group substituted with an n-hexyl group; a thiophene group substituted with a 2-ethylhexyl group; a thiophene group substituted with a 2-ethylhexylthioxy group; or a thiophene group substituted with fluorine and a 2-ethylhexyl group.

According to an exemplary embodiment of the present specification, Chemical Formula 1 is represented by any one of the following Chemical Formulae 1-16 to 1-29.

[Chemical Formula 1-16]

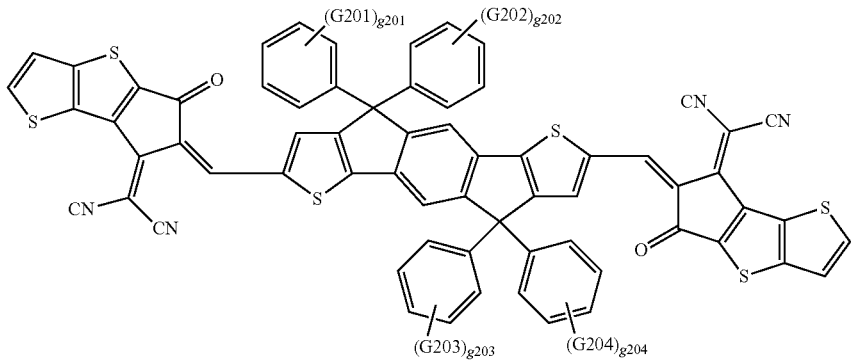

[Chemical Formula 1-17]

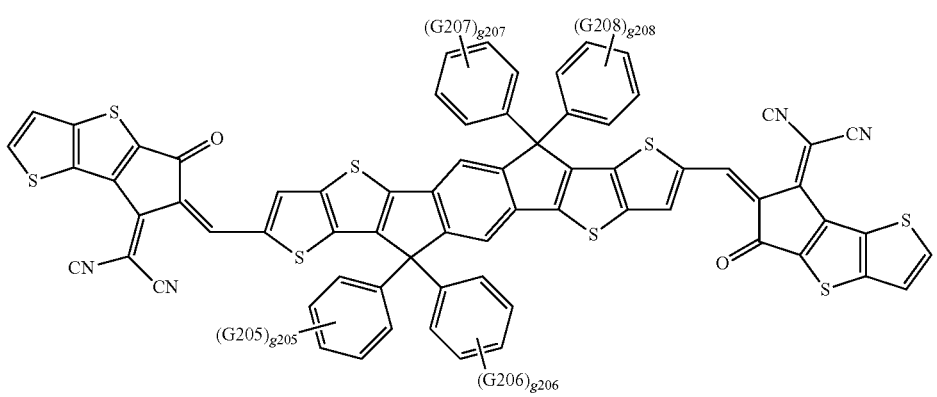

[Chemical Formula 1-18]
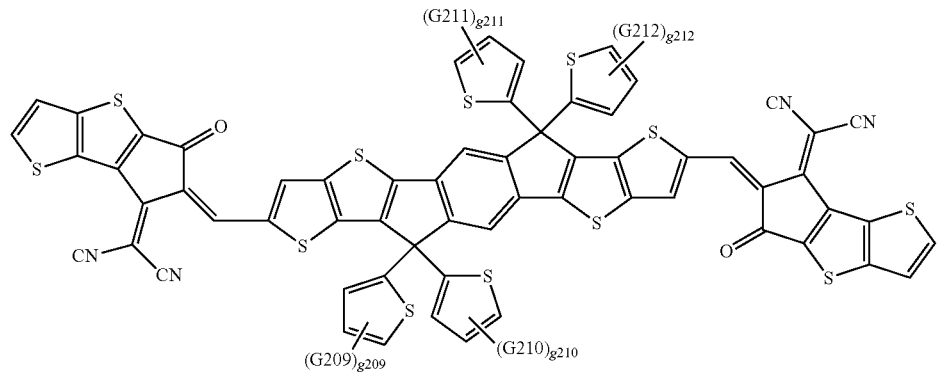
[Chemical Formula 1-19]
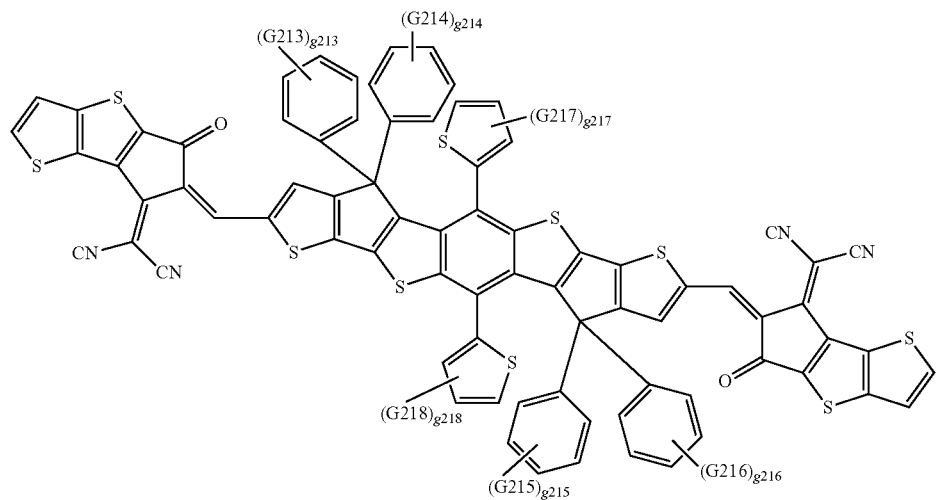
[Chemical Formula 1-20]
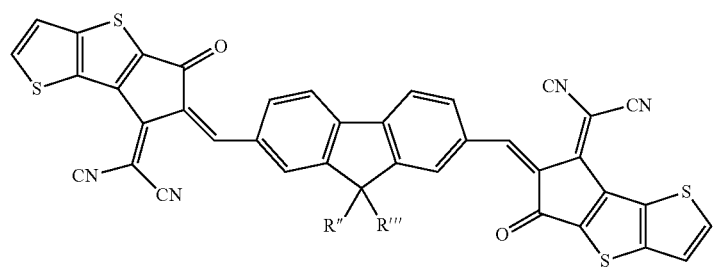
[Chemical Formula 1-21]
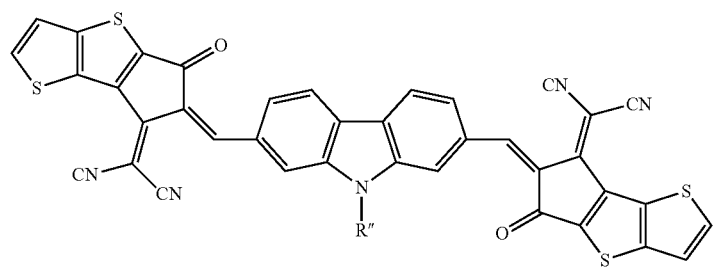

[Chemical Formula 1-22]
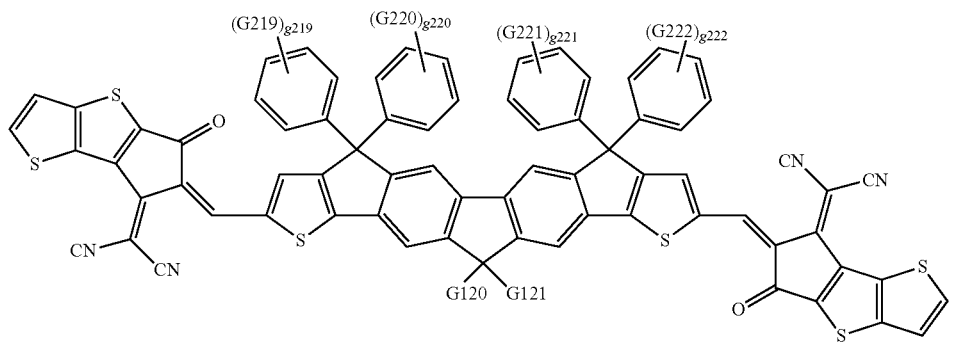
[Chemical Formula 1-23]
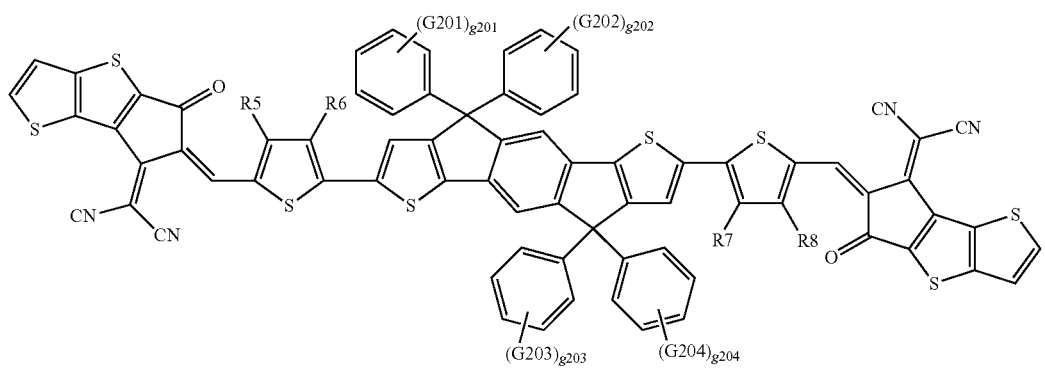
[Chemical Formula 1-24]
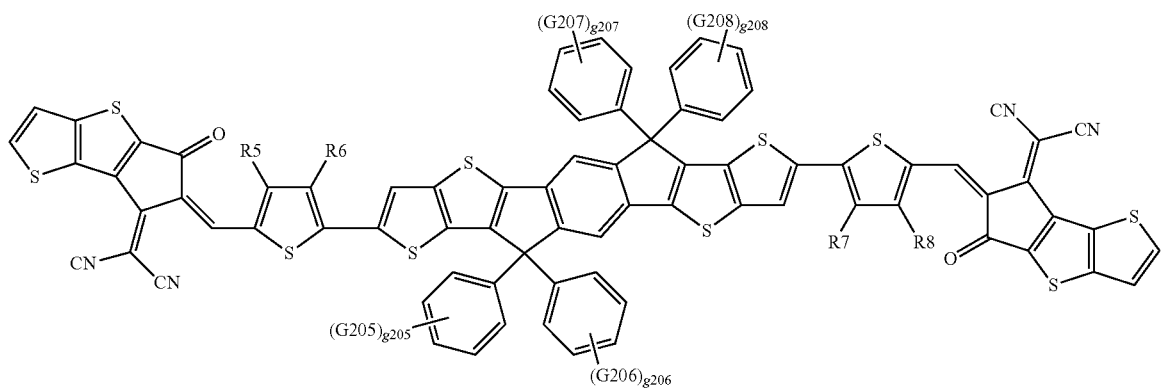
[Chemical Formula 1-25]
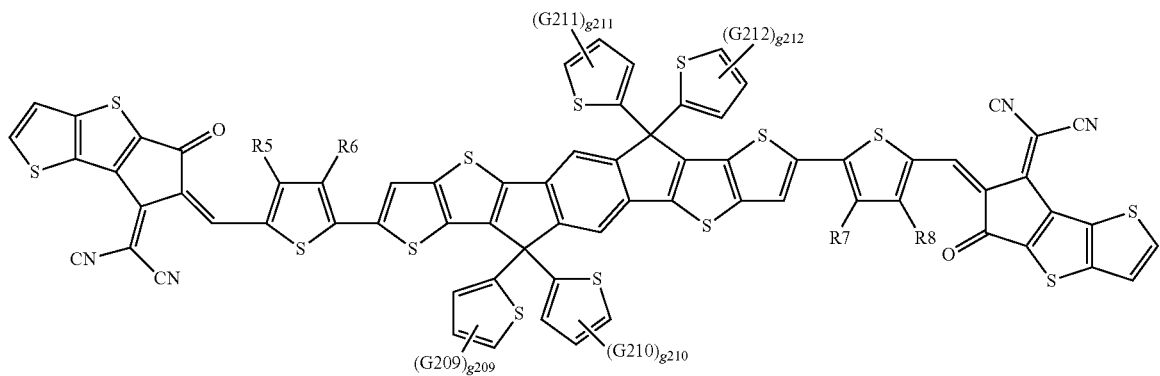

[Chemical Formula 1-26]
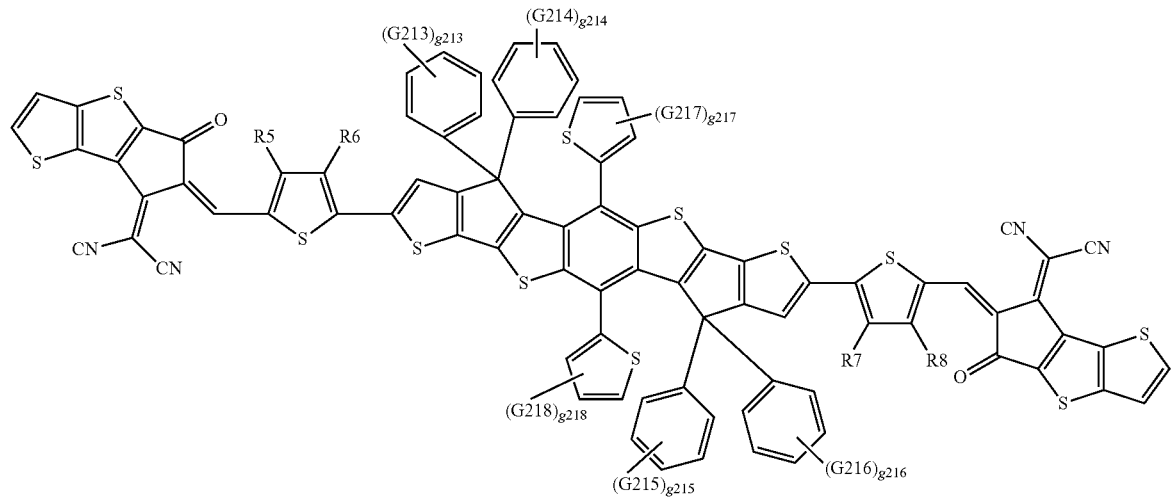
[Chemical Formula 1-27]
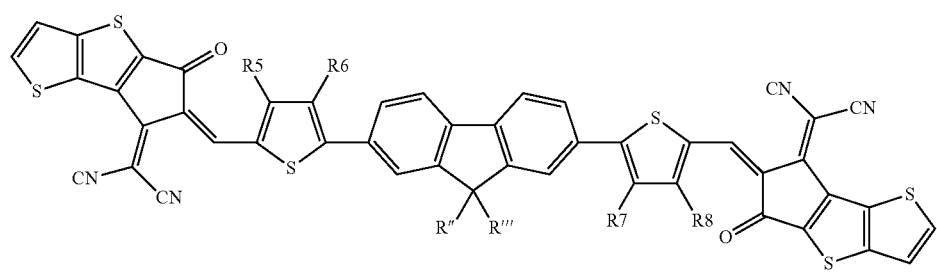
[Chemical Formula 1-28]
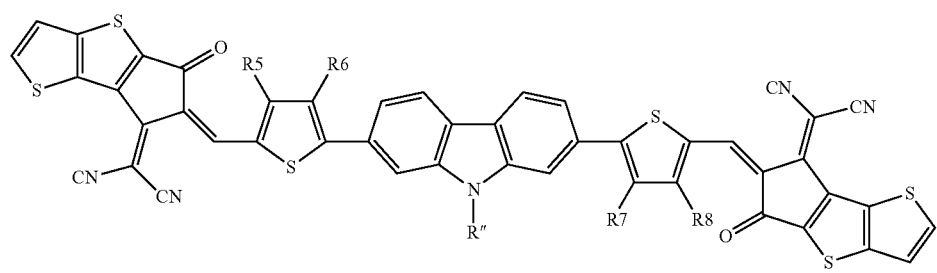
[Chemical Formula 1-29]
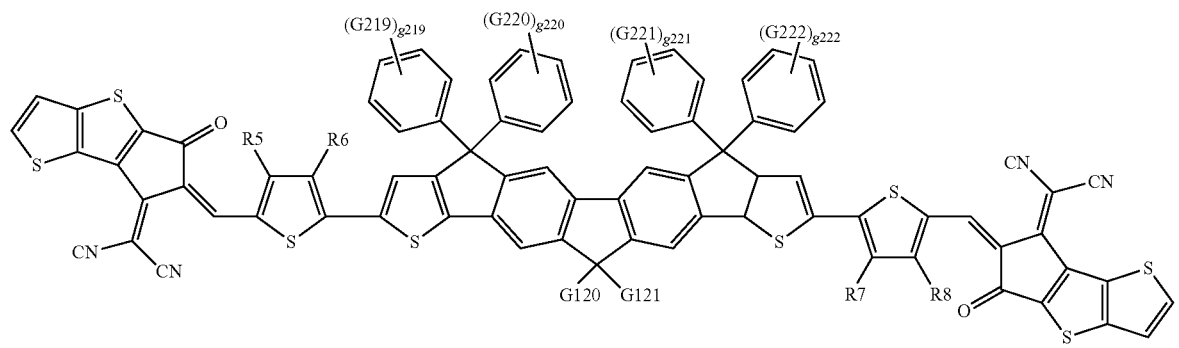

In Chemical Formulae 1-16 to 1-29,

R5 to R8 are the same as or different from each other, and are each independently hydrogen; a substituted or unsubstituted alkyl group; or a substituted or unsubstituted alkoxy group, G120, G121, and G201 to G222 are the same as or different from each other, and are each independently hydrogen; a halogen group; a substituted or unsubstituted alkyl group; or a substituted or unsubstituted thioalkoxy group, R" and R'" are the same as or different from each other, and are each independently a substituted or unsubstituted alkyl group, g201 to g208, g213 to g216, and g219 to g222 are each an integer of 1 to 5, g209 to g212, g217, and g218 are each an integer of 1 to 3, and when g201 to g222 are each 2 or more, two or more structures in the parenthesis are the same as or different from each other.

According to an exemplary embodiment of the present specification, when g201 to g222 are each 1, the structure in the parenthesis is a substituted or unsubstituted alkyl group; or a substituted or unsubstituted thioalkoxy group, and when g201 to g212 are each 2 or more, at least one of two or more structures in the parenthesis is a halogen group; a substituted or unsubstituted alkyl group; or a substituted or unsubstituted thioalkoxy group, and the others are hydrogen.

According to an exemplary embodiment of the present specification, G201 to G222 are the same as or different from each other, and are each independently a halogen group; a substituted or unsubstituted alkyl group; or a substituted or unsubstituted thioalkoxy group.

According to an exemplary embodiment of the present specification, G201 to G222 are the same as or different from each other, and are each independently a halogen group; an alkyl group; or a thioalkoxy group.

According to an exemplary embodiment of the present specification, G201 to G222 are fluorine; an n-hexyl group; a 2-ethylhexyl group; or a 2-ethylhexylthioxy group.

According to an exemplary embodiment of the present specification, when g201 to g222 are each 1, the structure in the parenthesis is an n-hexyl group; a 2-ethylhexyl group; or a 2-ethylhexylthioxy group, and when g201 to g222 are each 2 or more, at least one of two or more structures in the parenthesis is fluorine; an n-hexyl group; a 2-ethylhexyl group; or a 2-ethylhexylthioxy group, and the others are hydrogen.

According to an exemplary embodiment of the present specification, G201 to G222 are an n-hexyl group.

According to an exemplary embodiment of the present specification, G201 to G222 are a 2-ethylhexyl group.

According to an exemplary embodiment of the present specification, G201 to G222 are a 2-ethylhexylthoxy group.

According to an exemplary embodiment of the present specification, when g201 to g222 are each 1, the structure in the parenthesis is an n-hexyl group, and when g201 to g222 are each 2 or more, at least one of two or more structures in the parenthesis is an n-hexyl group, and the others are hydrogen.

According to an exemplary embodiment of the present specification, when g201 to g222 are each 1, the structure in the parenthesis is a 2-ethylhexyl group, and when g201 to g222 are each 2 or more, at least one of two or more structures in the parenthesis is a 2-ethylhexyl group, and the others are hydrogen.

According to an exemplary embodiment of the present specification, when g201 to g222 are each 1, the structure in the parenthesis is a 2-ethylhexylthioxy group, and when g201 to g222 are each 2 or more, at least one of two or more structures in the parenthesis is a 2-ethylhexylthoxy group, and the others are hydrogen.

According to an exemplary embodiment of the present specification, when g217 is 2, G217 are fluorine and a 2-ethylhexyl group.

According to an exemplary embodiment of the present specification, when g218 is 2, G218 are fluorine and a 2-ethylhexyl group.

According to an exemplary embodiment of the present specification, G120 and G121 are the same as or different from each other, and are each independently a substituted or unsubstituted alkyl group.

According to an exemplary embodiment of the present specification, G120 and G121 are the same as or different from each other, and are each independently a straight or branched alkyl group.

According to an exemplary embodiment of the present specification, G120 and G121 are an n-octyl group.

According to an exemplary embodiment of the present specification, Chemical Formula 1 is selected from the following compounds.

[Compound 1]

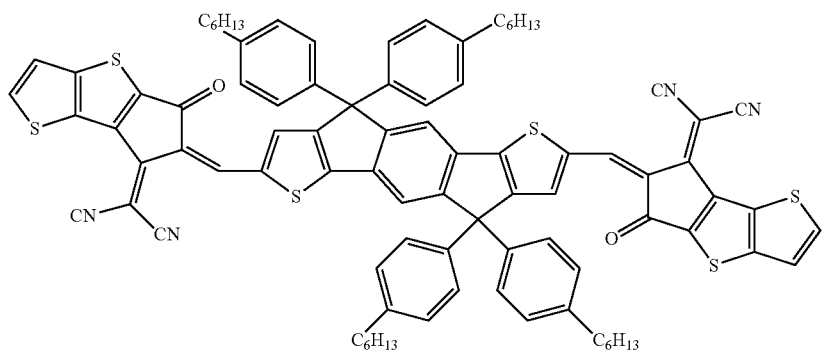

-continued
[Compound 2]
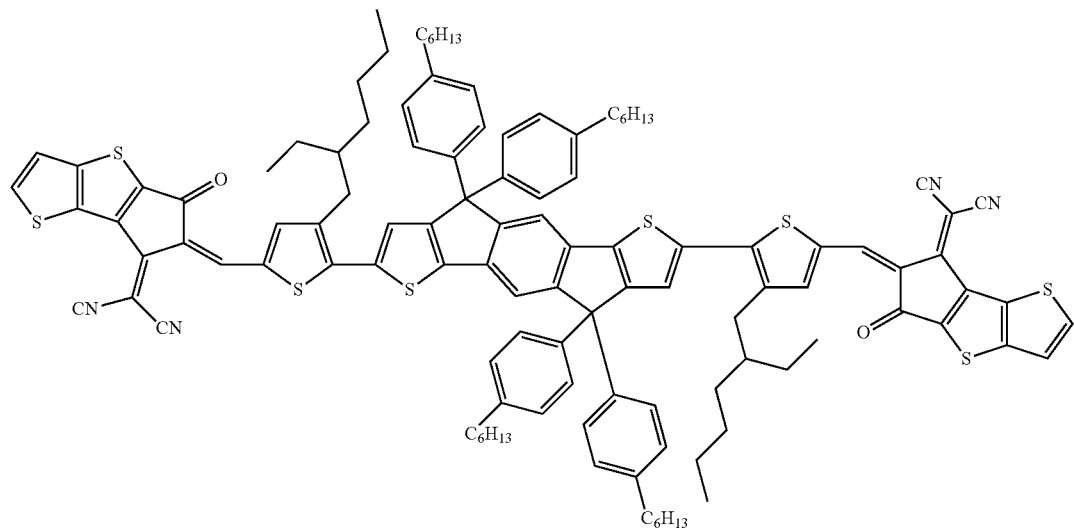
[Compound 3]
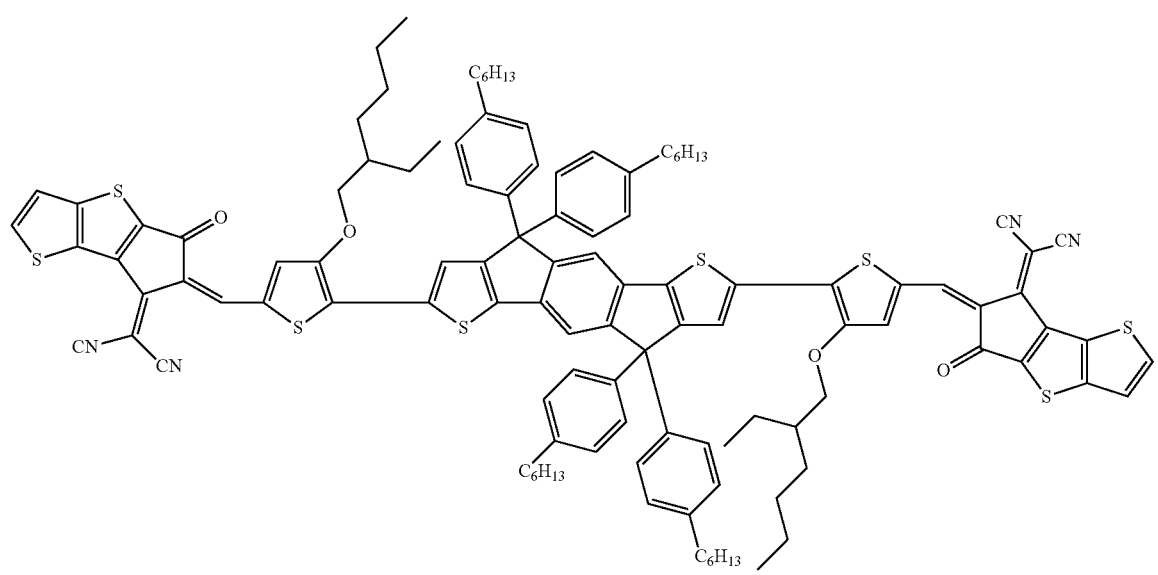
[Compound 4]
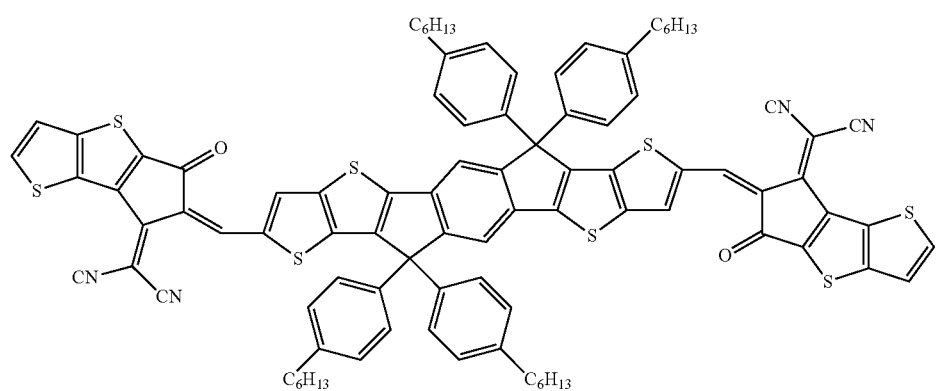

[Compound 5]
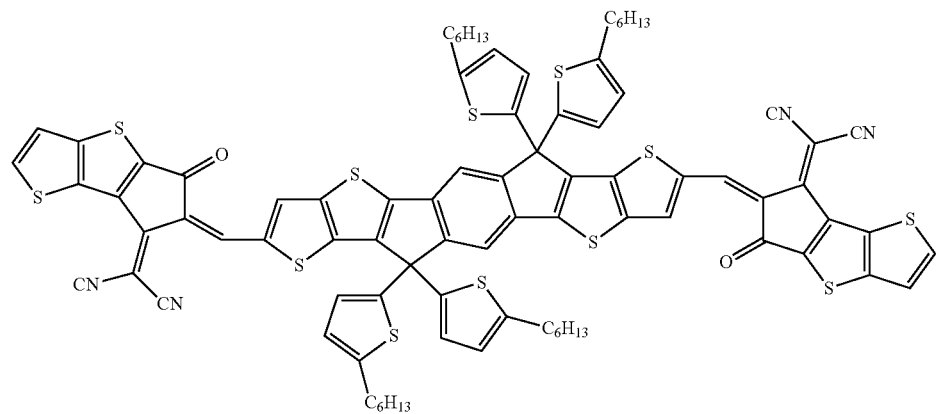
[Compound 6]
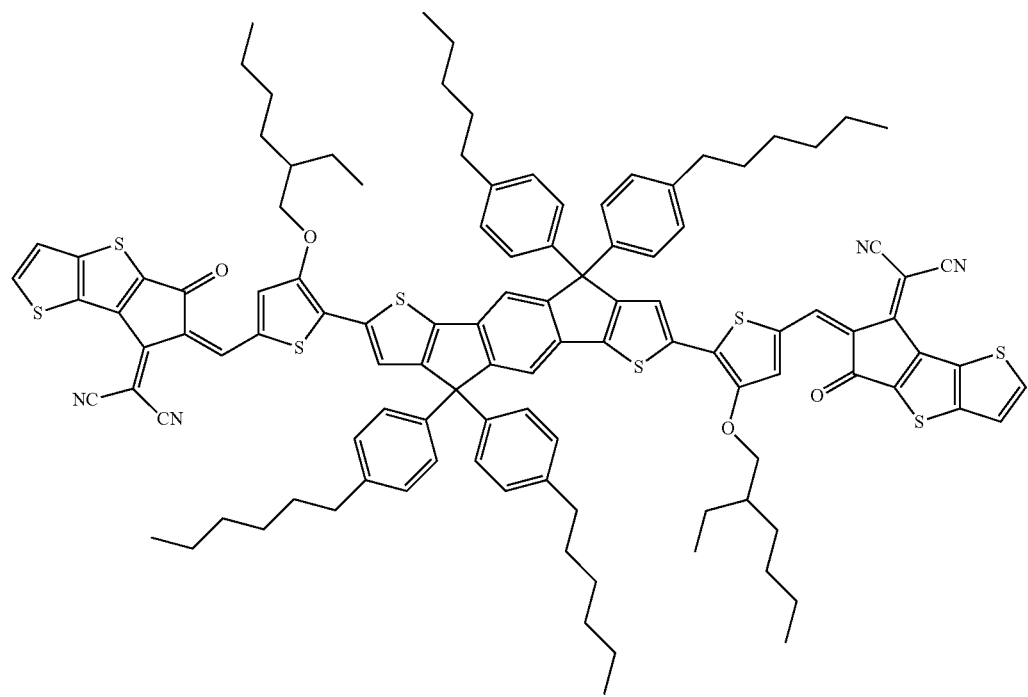

[Compound 7]
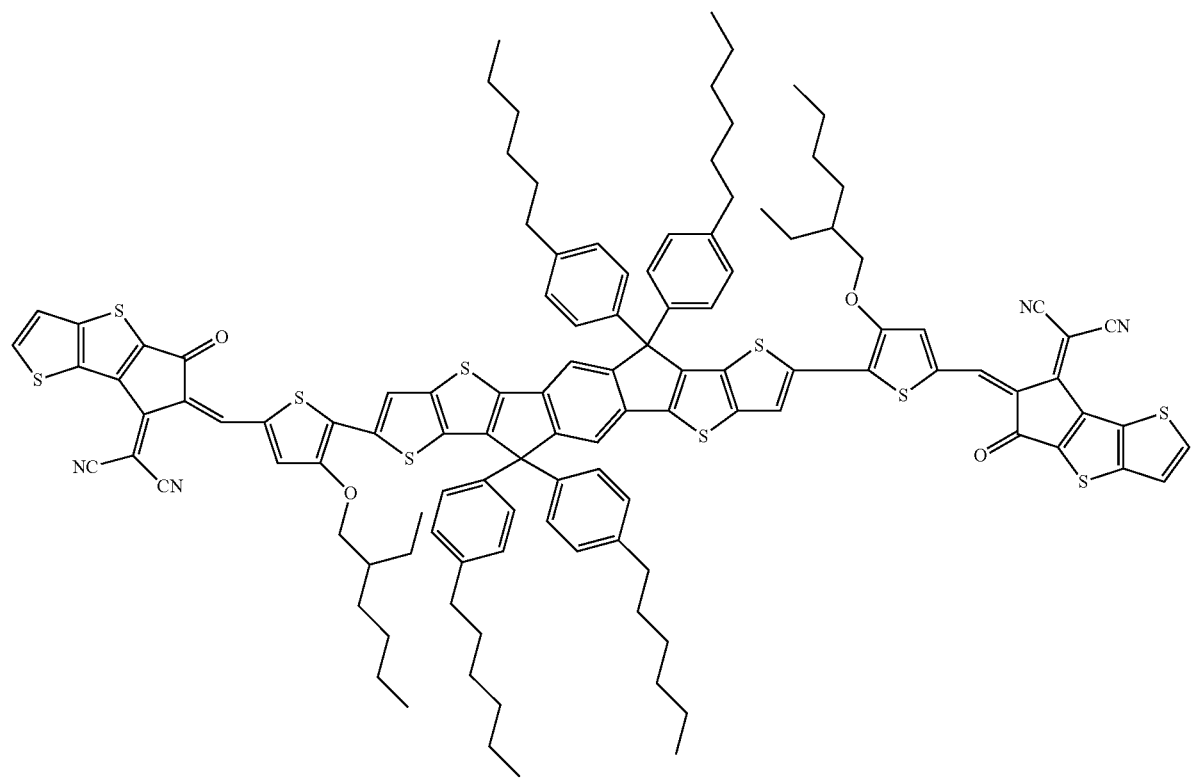
[Compound 8]
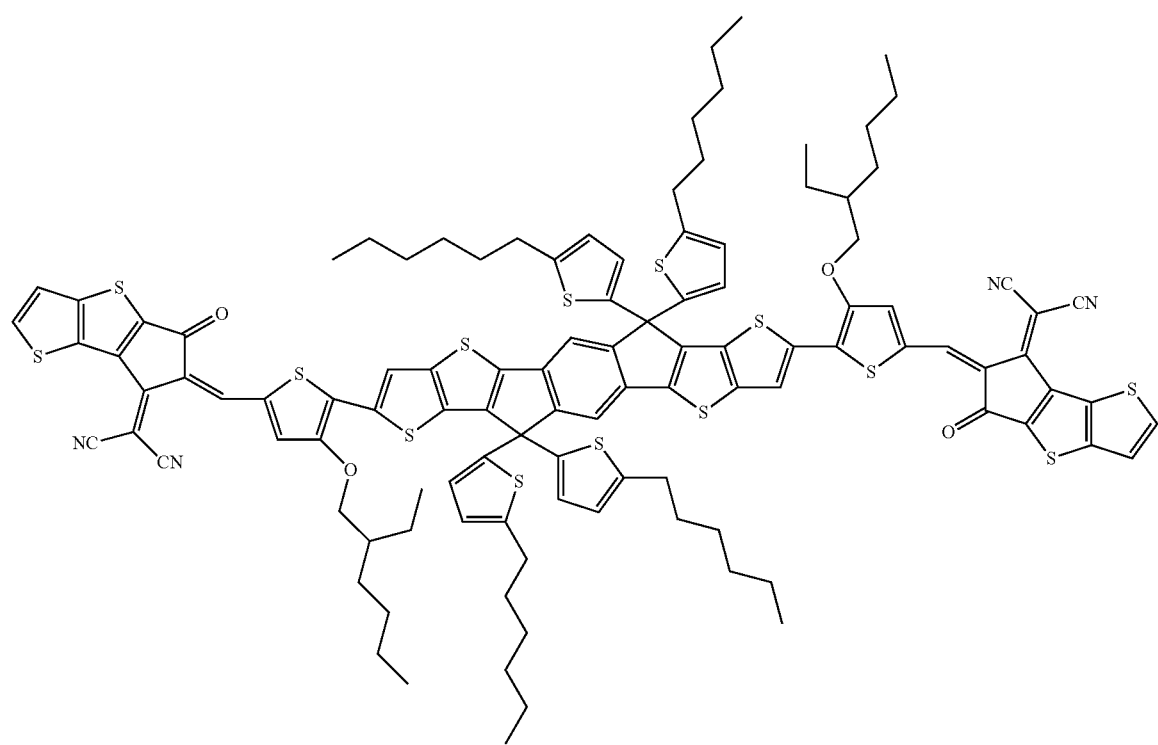

[Compound 9]
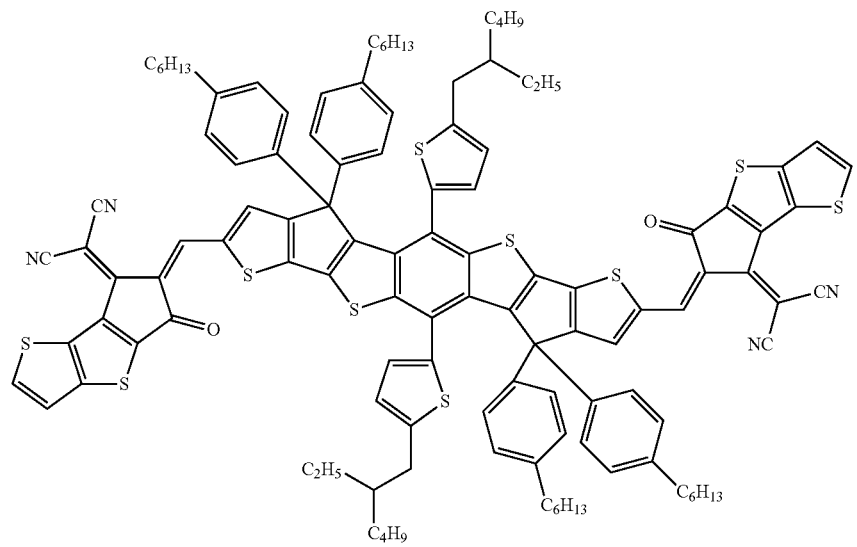
[Compound 10]
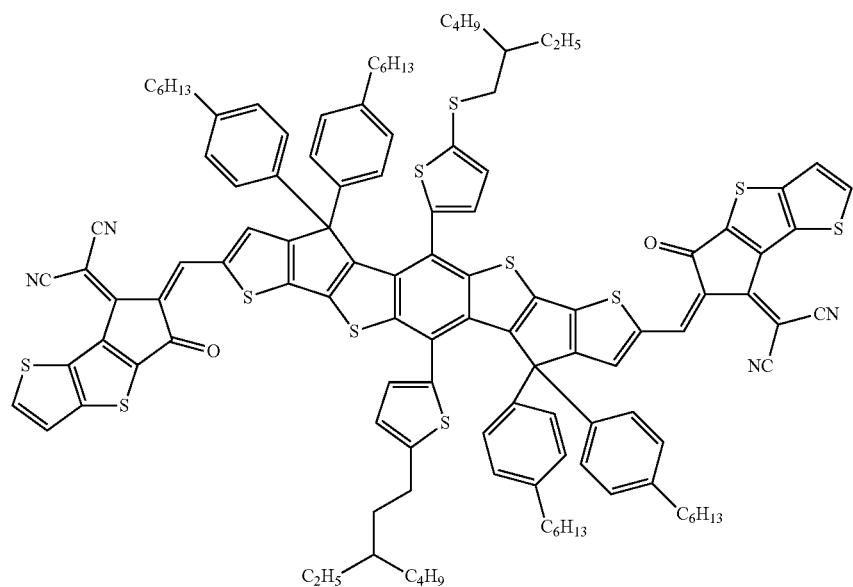
[Compound 11]
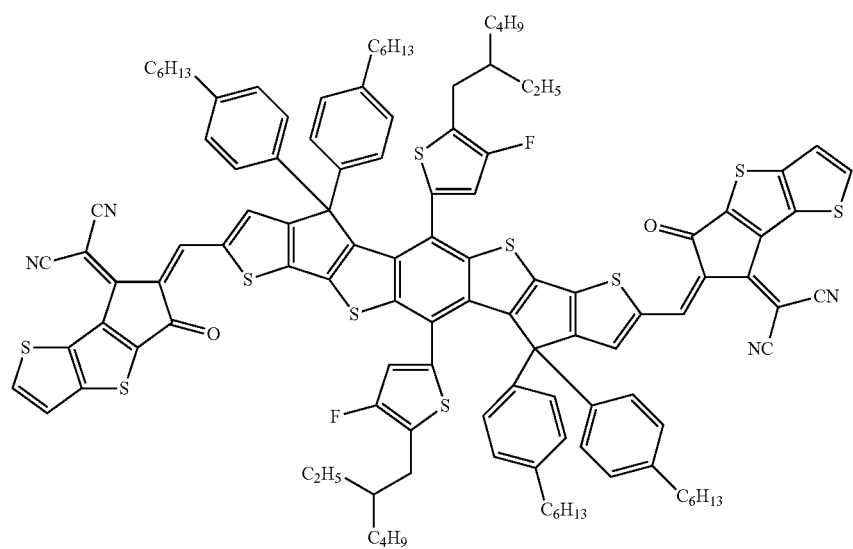

-continued

[Compound 12]

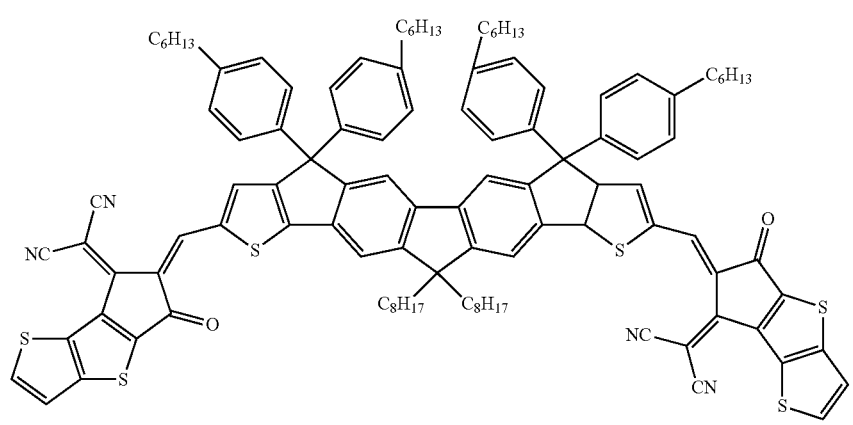

According to an exemplary embodiment of the present specification, the heterocyclic compound has a maximum absorption wavelength at 300 nm to 1,000 nm, and when the heterocyclic compound has the maximum absorption wavelength range, the heterocyclic compound may be used as a material for a photoactive layer of a near infra red (NIR) organic photoelectric device by absorbing light in a near infra red (NIR) region.

According to an exemplary embodiment of the present specification, the heterocyclic compound exhibits an absorption curve having a full width at half maximum of 100 nm to 1,000 nm in a film state.

Since the heterocyclic compound according to an exemplary embodiment of the present specification has a full width at half maximum within the range, there is an effect of absorbing light in visible light and near infra red (NIR) regions.

In the present specification, "a film state" does not mean a solution state, but means a state prepared in the form of a film by using the compound represented by Chemical Formula 1 alone or mixing the compound represented by Chemical Formula 1 with other components which does not affect the measurement of the full width at half maximum and the quantum efficiency.

In the present specification, the full width at half maximum means a width of the light emission peak when the height is half the maximum height at the maximum light emission peak of light emitted from the heterocyclic compound represented by Chemical Formula 1.

According to an exemplary embodiment of the present specification, the heterocyclic compound may have a LUMO energy level of 4 eV to 7 eV, and has a band gap of 1 eV to 3 eV. By having the LUMO level and the energy band gap within the ranges, the heterocyclic compound may be applied to an n-type organic material layer effectively absorbing light within a near infra red (NIR) region range, and accordingly, the heterocyclic compound may have high external quantum efficiency (EQE), thereby improving photoelectric conversion efficiency of an organic electronic device.

An exemplary embodiment of the present specification provides an organic electronic device including: a first electrode; a second electrode disposed to face the first electrode; and an organic material layer having one or more layers disposed between the first electrode and the second electrode, in which one or more layers of the organic material layer include the heterocyclic compound.

The organic electronic device according to an exemplary embodiment of the present specification includes a first electrode, a photoactive layer, and a second electrode. The organic electronic device may further include a substrate, a hole transporting layer, and/or an electron transporting layer.

FIG. 1 is a view illustrating an organic electronic device 100 according to an exemplary embodiment of the present specification, and according to FIG. 1, in the organic electronic device 100, light is incident from the sides of a first electrode 10 and/or a second electrode 20, so that when an active layer 30 absorbs light in the entire wavelength regions, excitons may be produced therein. The exciton is separated into a hole and an electron in the active layer 30, the separated hole moves to an anode side which is one of the first electrode 10 and the second electrode 20, and the separated electron moves to a cathode side which is the other of the first electrode 10 and the second electrode 20, so that an electric current may flow in the organic electronic device.

According to an exemplary embodiment of the present specification, the organic electronic device may further include an additional organic material layer. The organic electronic device may reduce the number of organic material layers by using an organic material which simultaneously has various functions.

According to an exemplary embodiment of the present specification, the first electrode is an anode, and the second electrode is a cathode. In another exemplary embodiment, the first electrode is a cathode, and the second electrode is an anode.

According to an exemplary embodiment of the present specification, in the organic electronic device, a cathode, a photoactive layer, and an anode may be arranged in this order, and an anode, a photoactive layer, and a cathode may be arranged in this order, but the arrangement order is not limited thereto.

In another exemplary embodiment, in the organic electronic device, an anode, a hole transporting layer, a photoactive layer, an electron transporting layer, and a cathode may also be arranged in this order, and a cathode, an electron transporting layer, a photoactive layer, a hole transporting layer, and an anode may also be arranged in this order, but the arrangement order is not limited thereto.

According to an exemplary embodiment of the present specification, the organic electronic device has a normal structure. In the normal structure, a substrate, an anode, an organic material layer including a photoactive layer, and a cathode may be stacked in this order.

According to an exemplary embodiment of the present specification, the organic electronic device has an inverted structure. In the inverted structure, a substrate, a cathode, an organic material layer including a photoactive layer, and an anode may be stacked in this order.

According to an exemplary embodiment of the present specification, the organic electronic device has a tandem structure.

The organic electronic device according to an exemplary embodiment of the present specification may include one or two or more photoactive layers. The tandem structure may include two or more photoactive layers.

In another exemplary embodiment, a buffer layer may be disposed between a photoactive layer and a hole transporting layer, or between a photoactive layer and an electron transporting layer. In this case, a hole injection layer may be further disposed between an anode and a hole transporting layer. Further, an electron injection layer may be further disposed between a cathode and an electron transporting layer.

According to an exemplary embodiment of the present specification, the photoactive layer includes an electron donor material and an electron acceptor material, and the electron acceptor material includes the heterocyclic compound.

According to an exemplary embodiment of the present specification, when the organic electronic device accepts a photon from an external light source, an electron and a hole are generated between an electron donor and an electron acceptor. The generated hole is transported to a positive electrode through an electron donor layer.

In addition, an organic electronic device in which the heterocyclic compound represented by Chemical Formula 1 is used as an n-type organic material layer (electron acceptor material) of a photoactive layer may be applied to most of the p-type organic materials (electron donor materials) having the maximum absorption wavelength in a visible light region, but the application range is not limited thereto.

According to an exemplary embodiment of the present specification, a material applied in the art may be used as the electron donor material, and the electron donor material may include, for example, one or more materials selected from the group consisting of poly 3-hexyl thiophene (P3HT), poly[N-9'-heptadecanyl-2,7-carbazole-alt-5,5-(4'-7'-di-2-thienyl-2',1',3'-benzothiadiazole)] (PCDTBT), poly[2,6-(4,4-bis-(2-ethylhexyl)-4H-cyclopenta[2,1-b;3,4-b']dithiophene)-alt-4,7-(2,1,3-benzothiadiazole)] (PCPDTBT), poly[2,7-(9,9-dioctyl-fluorene)-alt-5,5-(4,7-di 2-thienyl-2,1,3-benzothiadiazole)] (PFO-DBT), poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7 or PTB7-Th), poly[2,7-(9,9-dioctyl-dibenzosilole)-alt-4,7-bis(thiophen-2-yl)benzo-2,1,3-thiadiazole] (PSiF-DBT), and poly(benzodithiophene-benzotriazole) (PBDB-T).

According to an exemplary embodiment of the present specification, the photoactive layer includes an electron donor material and an electron acceptor material, and includes the electron donor material and the electron acceptor material at a weight ratio of 1:99 to 99:1.

According to an exemplary embodiment of the present specification, the photoactive layer includes an electron donor material and an electron acceptor material, and includes the electron donor material and the electron acceptor material at a weight ratio of 1:5 to 5:1.

According to an exemplary embodiment of the present specification, the electron donor and the electron acceptor constitute a bulk heterojunction (BHJ).

The bulk heterojunction means that an electron donor material and an electron acceptor material are mixed with each other in a photoactive layer.

In an exemplary embodiment of the present specification, the photoactive layer further includes an additive.

In an exemplary embodiment of the present specification, the additive has a molecular weight of 50 g/mol to 1,000 g/mol.

In another exemplary embodiment, the additive is an organic material having a boiling point of 30° C. to 300° C.

In the present specification, the organic material means a material including at least one or more carbon atoms.

In one exemplary embodiment, the additive may further include one or two additives among additives selected from the group consisting of 1,8-diiodooctane (DIO), 1-chloronaphthalene (1-CN), diphenylether (DPE), octane dithiol, and tetrabromothiophene.

According to an exemplary embodiment of the present specification, the photoactive layer has a bilayer thin film structure including an n-type organic material layer and a p-type organic material layer, and the n-type organic material layer includes the heterocyclic compound.

In the present specification, the substrate may be a glass substrate or a transparent plastic substrate having excellent transparency, surface smoothness, ease of handling, and water proof properties, but is not limited thereto, and is not limited as long as the substrate is a substrate typically used in an organic electronic device. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples thereof include: a metal, such as vanadium, chromium, copper, zinc, and gold, or an alloy thereof; a metal oxide, such as zinc oxide, indium oxide, indium tin oxide (ITO), and indium zinc oxide (IZO); a combination of metal and oxide, such as $ZnO:Al$ or $SnO_2:Sb$; an electrically conductive polymer, such as poly(3-methylthiophene), poly [3,4-(ethylene-1,2-dioxy)thiophene] (PEDT), polypyrrole, and polyaniline, and the like, but are not limited thereto.

A method of forming the anode electrode is not particularly limited, but the anode electrode may be formed, for example, by being applied onto one surface of a substrate using sputtering, e-beam, thermal deposition, spin coating, screen printing, inkjet printing, doctor blade, or a gravure printing method, or by being coated in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a heating plate at 100° C. to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film may be easily formed on an anode electrode, and the quality of the thin film may also be improved.

Examples of a pre-treatment technology for an anode electrode include a) a surface oxidation method using a parallel flat plate-type discharge, b) a method of oxidizing a surface through ozone produced by using UV rays in a vacuum state, c) an oxidation method using oxygen radicals produced by plasma, and the like.

One of the methods may be selected depending on the state of an anode electrode or a substrate. However, even though any method is used, it is preferred to commonly prevent oxygen from leaving from the surface of the anode electrode or the substrate, and maximally suppress moisture and organic materials from remaining. In this case, it is possible to maximize a substantial effect of the pre-treatment.

As a specific example, it is possible to use a method of oxidizing a surface through ozone produced by using UV. In this case, a patterned ITO substrate after being ultrasonically cleaned is baked on a hot plate and dried well, and then introduced into a chamber, and the patterned ITO substrate may be cleaned by ozone generated by reacting an oxygen gas with UV light by operating a UV lamp.

However, the surface modification method of the patterned ITO substrate in the present specification need not be particularly limited, and any method may be used as long as the method is a method of oxidizing a substrate.

The cathode electrode may be a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; and a multi-layer structured material such as LiF/Al, LiO$_2$/Al, LiF/Fe, Al:Li, Al:BaF$_2$, and Al:BaF$_2$:Ba, but are not limited thereto.

The cathode electrode may be deposited and formed in a thermal evaporator showing a vacuum degree of $5 \times 10^{-7}$ torr or less, but the forming method is not limited only to this method.

The hole transporting layer and/or electron transporting layer materials serve to efficiently transfer electrons and holes separated from a photoactive layer to an electrode, and the materials are not particularly limited.

The hole transporting layer material may be poly(3,4-ethylenediocythiophene) doped with poly(styrenesulfonic acid (PEDOT:PSS), molybdenum oxide (MoO$_x$); vanadium oxide (V$_2$O$_5$); nickel oxide (NiO); and tungsten oxide (WO$_x$), and the like, but is not limited thereto.

The electron transporting layer material may be electron-extracting metal oxides, and specific examples thereof include: a metal complex of 8-hydroxyquinoline; a complex including Alq$_3$; a metal complex including Liq; LiF; Ca; titanium oxide (TiO$_x$); zinc oxide (ZnO); and cesium carbonate (Cs$_2$CO$_3$), and the like, but are not limited thereto.

The photoactive layer may be formed by dissolving a photoactive material such as an electron donor and/or an electron acceptor in an organic solvent, and then applying the solution by a method such as spin coating, dip coating, screen printing, spray coating, doctor blade, and brush painting, but the forming method is not limited thereto.

According to an exemplary embodiment of the present specification, the organic electronic device is selected from the group consisting of an organic photoelectric device, an organic transistor, an organic solar cell, and an organic light emitting device.

According to an exemplary embodiment of the present specification, the organic electronic device is an organic solar cell.

According to an exemplary embodiment of the present specification, the organic electronic device is an organic photoelectric device.

Specifically, the organic photoelectric device according to an exemplary embodiment of the present specification may be applied to an organic image sensor, an organic light detector, an organic light sensor, and the like, but the application range is not limited thereto.

An exemplary embodiment of the present specification provides an organic image sensor including the organic electronic device.

The organic image sensor according to an exemplary embodiment of the present specification may be applied to an electronic device, and may be applied to, for example, a mobile phone, a digital camera, and the like, but the application range is not limited thereto.

MODE FOR INVENTION

A preparation method of the heterocyclic compound and the manufacture of an organic electronic device including the same will be described in detail in the following Preparation Examples and Examples. However, the following Examples are provided for exemplifying the present specification, and the scope of the present specification is not limited thereby.

Preparation Example 1. Preparation of Compound 2

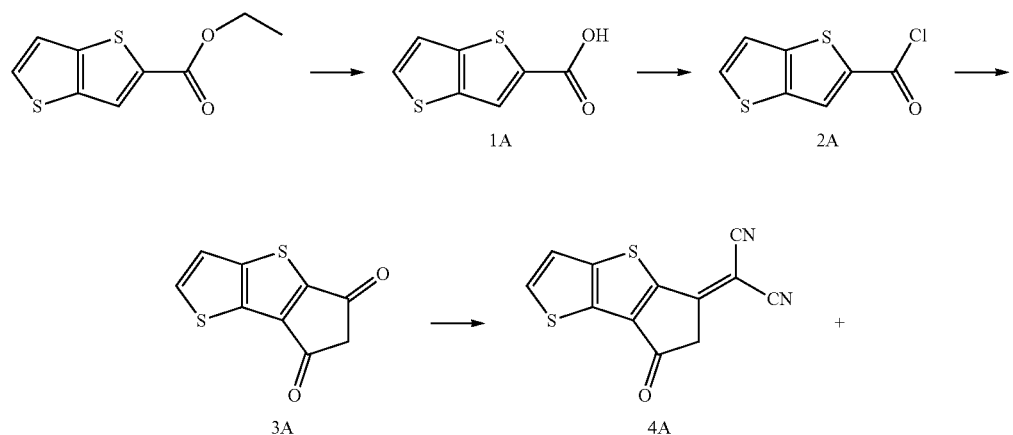

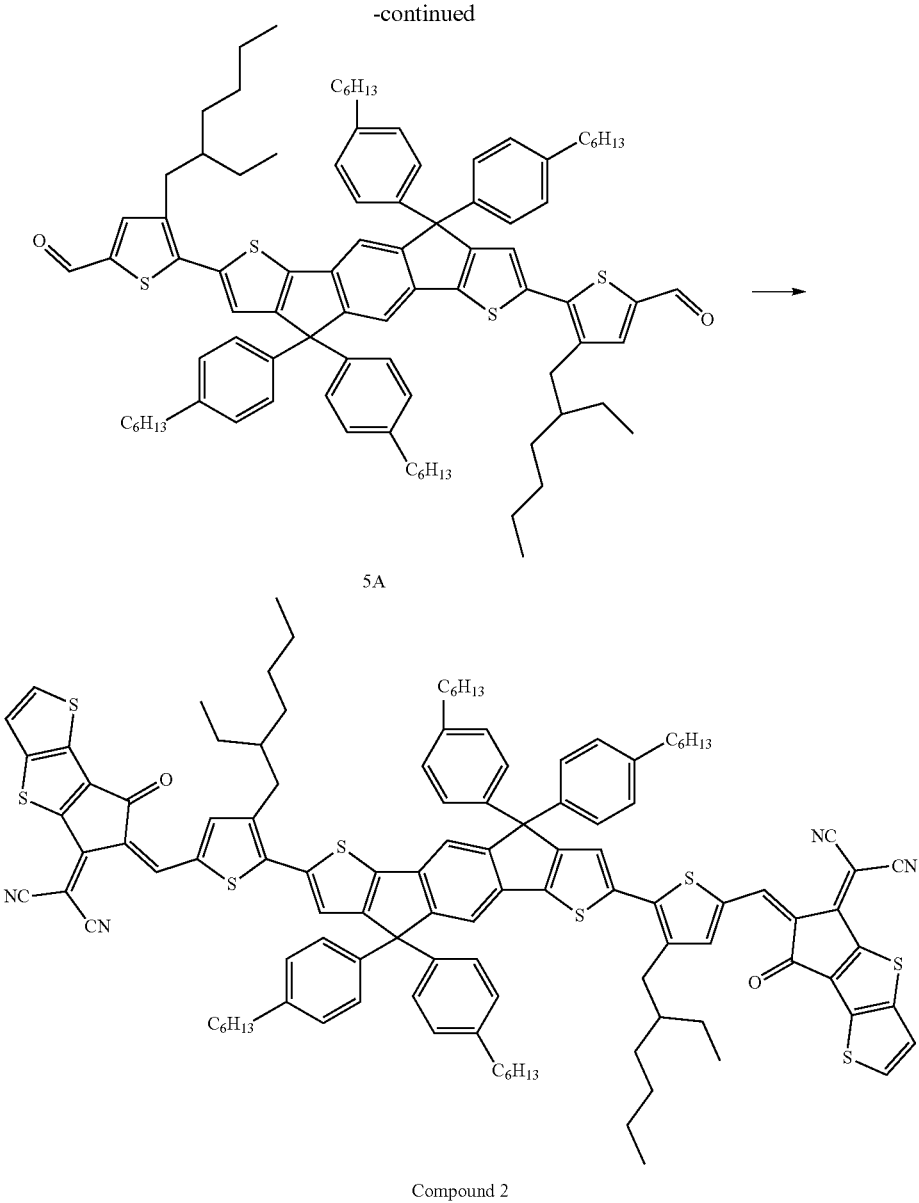

Compound 2

1) Preparation of Compound 1A

After 21.39 g of ethyl thieno[3,2-b]thiophene-2-carboxylate and 200 mL of tetrahydrofuran were injected into a 500-mL round flask, 8.39 g (1.5 eq) of NaOH was dissolved in 200 mL of distilled water, the resulting solution was injected thereinto, and then the temperature was adjusted to 60° C. Thereafter, the resulting mixture was refluxed for 2 hours, the reaction was terminated through a 1 M aqueous HCl solution, and then the produced solid was filtered through distilled water, thereby obtaining Compound 1A. [1H NMR 500 MHz, CDCl$_3$] 8.095 (s, 1H), 7.653 (d, 1H), 7.323 (d, 1H)

2) Preparation of Compound 2A 1.00 g of Compound 1A and 200 mL of chloroform were injected into a 500-mL round flask, and then 15.76 mL (1.5 eq) of thionyl chloride was slowly injected thereinto. Thereafter, a catalytic amount of dimethylformamide was injected thereto, and then the resulting mixture was refluxed for 1 hour by adjusting the temperature to 65° C. Thereafter, the solvent was removed, thereby obtaining Compound 2A. [1H NMR 500 MHz, CDCl$_3$] 8.096 (s, 1H), 7.742 (d, 1H), 7.308 (d, 1H)

3) Preparation of Compound 3A 29.60 g (1.00 eq) of aluminum chloride and 21.59 mL (4.5 eq) of malonyl dichloride were put into 200 mL of dichloromethane in a 500-mL round flask, and then the resulting mixture was stirred for 10 minutes and activated. Thereafter, Compound 2A was dissolved in 50 mL of dichloromethane, the resulting solution was slowly injected thereinto, and then the mixture was refluxed at 60° C. for 12 hours. After the reaction was terminated through a 10% aqueous oxalic acid solution, extraction was performed by using ethyl acetate, and then the solvent was removed, thereby obtaining Compound 3A. [1H NMR 500 MHz, CDCl$_3$] 7.843 (d, 1H), 7.447 (d, 1H), 3.512 (s, 2H)

4) Preparation of Compound 4A 1 g of Compound 3A, 0.59 g (1.5 eq) of sodium acetate, and 0.65 g (1.5 eq) of malononitrile were put into 100 mL of dimethyl sulfoxide in a 500-mL round flask, and then the resulting mixture was stirred at room temperature for 1 hour. Thereafter, the product was acidified through an aqueous HCl solution, and then the produced solid was filtered, and Compound 4A was obtained through column chromatography. [1H NMR 500 MHz, CDCl$_3$] 7.885 (d, 1H), 7.469 (d, 1H), 3.945 (s, 2H)

5) Preparation of Compound 2

After 100 mg of Compound 5A and 75 mg (4 eq) of Compound 4A were dissolved in 50 mL of chloroform in a 100-mL round flask, 0.6 mL of pyridine was injected thereinto, and then the resulting mixture was refluxed at 70° C. for 12 hours. An extraction was performed by using chloroform, and then the solvent was removed, thereby obtaining Compound 2.

FIG. 2 is a view illustrating a 1H-NMR spectrum of Compound 2 according to an exemplary embodiment of the present specification.

Preparation Example 2. Preparation of Compound 3

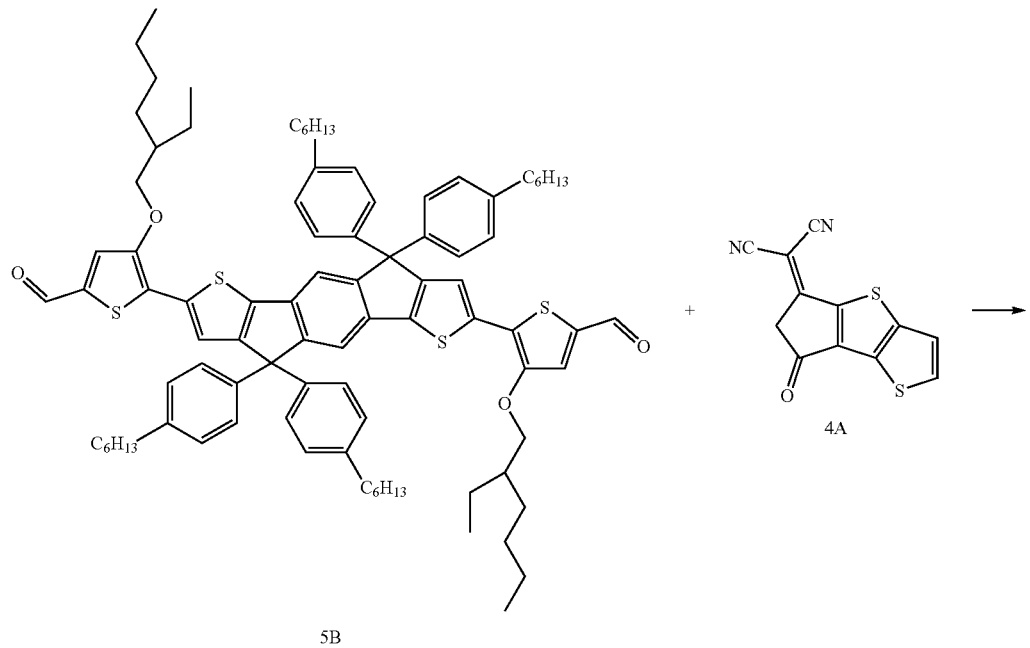

5B

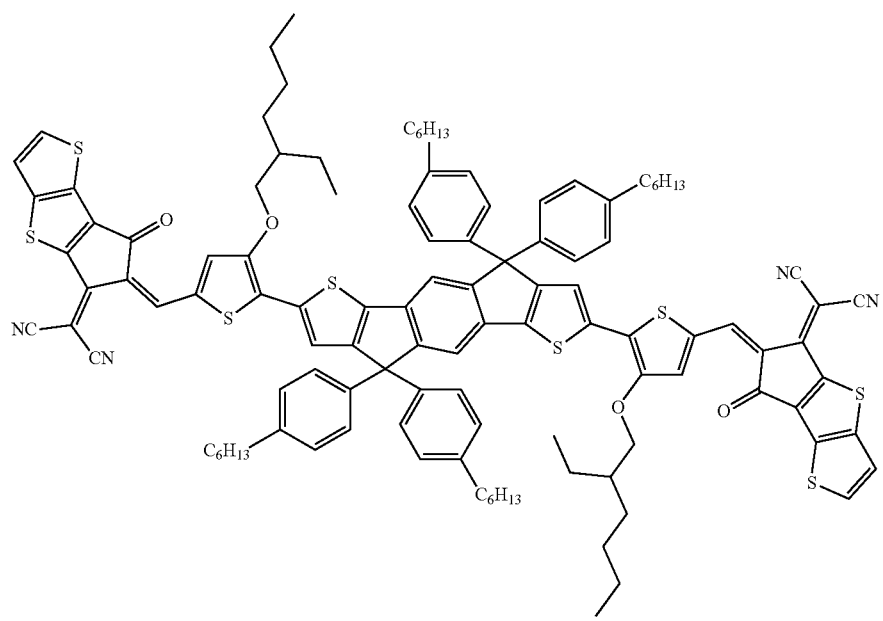

Compound 3

After 500 mg of Compound 5B and 370 mg (4 eq) of Compound 4A were dissolved in 50 mL of chloroform in a 100-mL round flask, 0.6 mL of pyridine was injected thereinto, and then the resulting mixture was refluxed at 70° C. for 12 hours. An extraction was performed by using chloroform, and then the solvent was removed, thereby obtaining Compound 3.

1H NMR: 8.25 (s, 2H), 7.89 (d, 2H), 7.28 (s, 2H), 7.26 (s, 2H), 7.18 (m, 4H), 7.14 (d, 8H), 7.08 (d, 8H), 2.94 (d, 4H), 2.62 (t, 8H), 1.87 (m, 2H), 1.22 (m, 48H), 0.94 (m, 36H).

Comparative Example 1-1. Manufacture of Organic Solar Cell

A composite solution was prepared by dissolving the following compound PBDB-T and the following Comparative Example Compound 1 (IEIC) at a ratio of 1:1 in chlorobenzene (CB). In this case, the concentration was adjusted to 4 wt %, and the organic solar cell was made to have an inverted structure of ITO/ZnO NP/a photoactive layer/MoO$_3$/Ag.

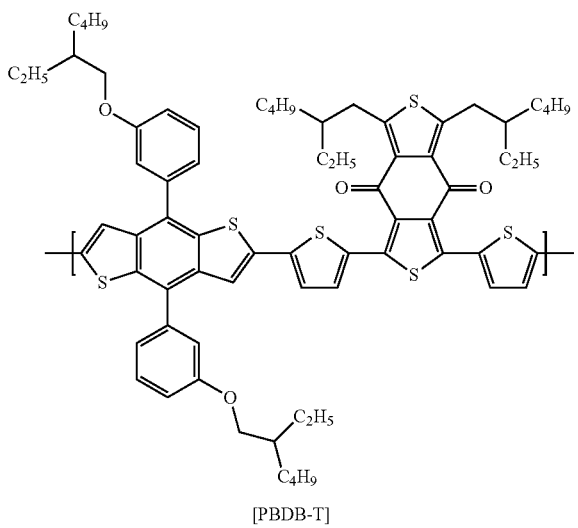

[PBDB-T]

Comparative Example Compound 1 (IEIC)

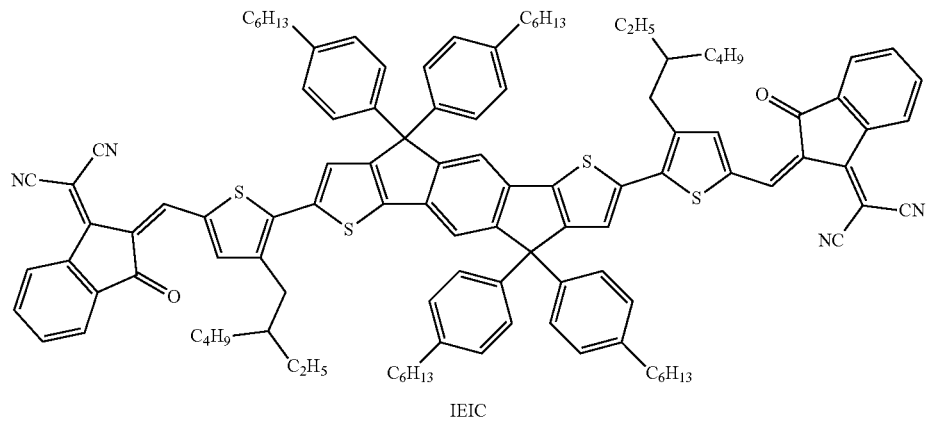

IEIC

A glass substrate (11.5Ω/□) coated with ITO with 1.5 cm×1.5 cm as a bar type was ultrasonically washed by using distilled water, acetone, and 2-propanol, the ITO surface was treated with ozone for 10 minutes, and then ZnO NP (2.5 wt % of ZnO nanograde N-10 in 1-butanol, filtered by a 0.45 μm PTFE) was prepared, the ZnO NP solution was spin-coated at 4,000 rpm for 40 seconds, and then the remaining solvent was removed by performing a heat treatment at 80° C. for 10 minutes, thereby completing an electron transporting layer. In order to coat the photoactive layer, the composite solution of the following compound PBDB-T and the following Comparative Example Compound 1 was spin-coated at 70° C. and 1,000 rpm for 25 seconds. In a thermal evaporator, MoO$_3$ was thermally deposited to have a thickness of 10 nm at a rate of 0.2 Å/s under 10$^{-7}$ Torr, thereby manufacturing a hole transporting layer. After the manufacture in the above order, Ag was deposited to have a thickness of 100 nm at a rate of 1 Å/s in a thermal evaporator, thereby manufacturing an organic solar cell having an inverted structure.

Comparative Example 1-2. Manufacture of Organic Solar Cell

An organic solar cell was manufactured in the same manner as in Comparative Example 1-1, except that in Comparative Example 1-1, the composite solution of the compound PBDB-T and Comparative Example Compound 1 was spin-coated at 1,200 rpm instead of 1,000 rpm.

Comparative Example 1-3. Manufacture of Organic Solar Cell

An organic solar cell was manufactured in the same manner as in Comparative Example 1-1, except that in Comparative Example 1-1, the composite solution of the compound PBDB-T and Comparative Example Compound 1 was spin-coated at 1,400 rpm instead of 1,000 rpm.

Comparative Example 1-4. Manufacture of Organic Solar Cell

An organic solar cell was manufactured in the same manner as in Comparative Example 1-1, except that in Comparative Example 1-1, the composite solution of the compound PBDB-T and Comparative Example Compound 1 was spin-coated at 1,600 rpm instead of 1,000 rpm.

Comparative Example 2-1. Manufacture of Organic Solar Cell

An organic solar cell was manufactured in the same manner as in Comparative Example 1-1, except that in Comparative Example 1-1, the composite solution of the compound PBDB-T and Comparative Example Compound 1 were used at a ratio of 1:1.5 instead of 1:1.

Comparative Example 2-2. Manufacture of Organic Solar Cell

An organic solar cell was manufactured in the same manner as in Comparative Example 1-2, except that in Comparative Example 1-2, the composite solution of the compound PBDB-T and Comparative Example Compound 1 were used at a ratio of 1:1.5 instead of 1:1.

Comparative Example 2-3. Manufacture of Organic Solar Cell

An organic solar cell was manufactured in the same manner as in Comparative Example 1-3, except that in Comparative Example 1-3, the composite solution of the compound PBDB-T and Comparative Example Compound 1 were used at a ratio of 1:1.5 instead of 1:1.

Comparative Example 2-4. Manufacture of Organic Solar Cell

An organic solar cell was manufactured in the same manner as in Comparative Example 1-4, except that in Comparative Example 1-4, the composite solution of the compound PBDB-T and Comparative Example Compound 1 were used at a ratio of 1:1.5 instead of 1:1.

Comparative Example 3-1. Manufacture of Organic Solar Cell

An organic solar cell was manufactured in the same manner as in Comparative Example 1-1, except that in Comparative Example 1-1, the composite solution of the compound PBDB-T and Comparative Example Compound 1 were used at a ratio of 1:2 instead of 1:1.

Comparative Example 3-2. Manufacture of Organic Solar Cell

An organic solar cell was manufactured in the same manner as in Comparative Example 1-2, except that in Comparative Example 1-2, the composite solution of the compound PBDB-T and Comparative Example Compound 1 were used at a ratio of 1:2 instead of 1:1.

Comparative Example 3-3. Manufacture of Organic Solar Cell

An organic solar cell was manufactured in the same manner as in Comparative Example 1-3, except that in Comparative Example 1-3, the composite solution of the compound PBDB-T and Comparative Example Compound 1 were used at a ratio of 1:2 instead of 1:1.

Comparative Example 3-4. Manufacture of Organic Solar Cell

An organic solar cell was manufactured in the same manner as in Comparative Example 1-4, except that in Comparative Example 1-4, the composite solution of the compound PBDB-T and Comparative Example Compound 1 were used at a ratio of 1:2 instead of 1:1.

Example 1-1. Manufacture of Organic Solar Cell

An organic solar cell was manufactured in the same manner as in Comparative Example 1-1, except that in Comparative Example 1-1, Compound 2 was used instead of Comparative Example Compound 1.

Example 1-2. Manufacture of Organic Solar Cell

An organic solar cell was manufactured in the same manner as in Comparative Example 1-2, except that in Comparative Example 1-2, Compound 2 was used instead of Comparative Example Compound 1.

Example 1-3. Manufacture of Organic Solar Cell

An organic solar cell was manufactured in the same manner as in Comparative Example 1-3, except that in Comparative Example 1-3, Compound 2 was used instead of Comparative Example Compound 1.

Example 1-4. Manufacture of Organic Solar Cell

An organic solar cell was manufactured in the same manner as in Comparative Example 1-4, except that in Comparative Example 1-4, Compound 2 was used instead of Comparative Example Compound 1.

Example 2-1. Manufacture of Organic Solar Cell

An organic solar cell was manufactured in the same manner as in Example 1-1, except that in Example 1-1, the compound PBDB-T and Compound 2 were used at a ratio of 1:1.5 instead of 1:1.

Example 2-2. Manufacture of Organic Solar Cell

An organic solar cell was manufactured in the same manner as in Example 1-2, except that in Example 1-2, the compound PBDB-T and Compound 2 were used at a ratio of 1:1.5 instead of 1:1.

Example 2-3. Manufacture of Organic Solar Cell

An organic solar cell was manufactured in the same manner as in Example 1-3, except that in Example 1-3, the compound PBDB-T and Compound 2 were used at a ratio of 1:1.5 instead of 1:1.

Example 2-4. Manufacture of Organic Solar Cell

An organic solar cell was manufactured in the same manner as in Example 1-4, except that in Example 1-4, the compound PBDB-T and Compound 2 were used at a ratio of 1:1.5 instead of 1:1.

Example 3-1. Manufacture of Organic Solar Cell

An organic solar cell was manufactured in the same manner as in Example 1-1, except that in Example 1-1, the compound PBDB-T and Compound 2 were used at a ratio of 1:2 instead of 1:1.

Example 3-2. Manufacture of Organic Solar Cell

An organic solar cell was manufactured in the same manner as in Example 1-2, except that in Example 1-2, the compound PBDB-T and Compound 2 were used at a ratio of 1:2 instead of 1:1.

Example 3-3. Manufacture of Organic Solar Cell

An organic solar cell was manufactured in the same manner as in Example 1-3, except that in Example 1-3, the compound PBDB-T and Compound 2 were used at a ratio of 1:2 instead of 1:1.

Example 3-4. Manufacture of Organic Solar Cell

An organic solar cell was manufactured in the same manner as in Example 1-4, except that in Example 1-4, the compound PBDB-T and Compound 2 were used at a ratio of 1:2 instead of 1:1.

Photoelectric conversion characteristics of the organic solar cells manufactured in Examples 1-1 to 1-4, 2-1 to 2-4, and 3-1 to 3-4 and Comparative Examples 1-1 to 1-4, 2-1 to 2-4, and 3-1 to 3-4 were measured under a condition of 100 mW/cm$^2$ (AM 1.5), and the results are shown in the following Table 1.

FIG. 3 is a view illustrating UV-vis absorption spectra in a film state with respect to Compound 2 according to an exemplary embodiment of the present specification and IEIC which is Comparative Example Compound 1, and FIG. 4 is a view illustrating HOMO/LUMO energy levels of Compound 2 according to an exemplary embodiment of the present specification and IEIC which is Comparative Example Compound 1.

TABLE 1

| | Spin-speed (rpm) | $V_{oc}$ (V) | $J_{sc}$ (mA/cm$^2$) | FF | η (%) | Average η (%) |
|---|---|---|---|---|---|---|
| Comparative Example 1-1 | 1000 | 0.874 | 6.998 | 0.350 | 2.14 | 2.33 |
| | | 0.869 | 7.141 | 0.406 | 2.52 | |
| Comparative Example 1-2 | 1200 | 0.874 | 7.863 | 0.452 | 3.11 | 2.96 |
| | | 0.874 | 7.978 | 0.404 | 2.81 | |
| Comparative Example 1-3 | 1400 | 0.881 | 7.969 | 0.426 | 2.99 | 3.04 |
| | | 0.866 | 7.893 | 0.451 | 3.08 | |
| Comparative Example 1-4 | 1600 | 0.879 | 8.177 | 0.459 | 3.30 | 3.37 |
| | | 0.876 | 7.920 | 0.496 | 3.44 | |
| Comparative Example 2-1 | 1000 | 0.892 | 10.290 | 0.484 | 4.45 | 4.37 |
| | | 0.854 | 9.903 | 0.507 | 4.29 | |
| Comparative Example 2-2 | 1200 | 0.892 | 10.677 | 0.515 | 4.91 | 5.07 |
| | | 0.888 | 10.344 | 0.569 | 5.23 | |
| Comparative Example 2-3 | 1400 | 0.894 | 11.275 | 0.524 | 5.29 | 5.34 |
| | | 0.886 | 10.443 | 0.582 | 5.39 | |
| Comparative Example 2-4 | 1600 | 0.887 | 10.699 | 0.574 | 5.45 | 5.48 |
| | | 0.875 | 10.380 | 0.607 | 5.51 | |
| Comparative Example 3-1 | 1000 | 0.895 | 14.071 | 0.577 | 7.27 | 7.26 |
| | | 0.890 | 14.192 | 0.574 | 7.25 | |
| Comparative Example 3-2 | 1200 | 0.911 | 14.299 | 0.602 | 7.84 | 7.84 |
| Comparative Example 3-3 | 1400 | 0.897 | 13.921 | 0.637 | 7.96 | 8.01 |
| | | 0.896 | 14.437 | 0.623 | 8.05 | |
| Comparative Example 3-4 | 1600 | 0.901 | 14.074 | 0.623 | 7.90 | 7.83 |
| | | 0.896 | 13.543 | 0.639 | 7.76 | |
| Example 1-1 | 1000 | 0.895 | 15.543 | 0.623 | 8.67 | 8.59 |
| | | 0.895 | 15.491 | 0.613 | 8.50 | |
| Example 1-2 | 1200 | 0.903 | 15.429 | 0.625 | 8.71 | 8.88 |
| | | 0.898 | 15.984 | 0.630 | 9.04 | |
| Example 1-3 | 1400 | 0.897 | 15.033 | 0.605 | 8.16 | 8.55 |
| | | 0.898 | 15.541 | 0.639 | 8.93 | |
| Example 1-4 | 1600 | 0.901 | 14.506 | 0.648 | 8.47 | 8.46 |
| | | 0.899 | 14.553 | 0.645 | 8.44 | |
| Example 2-1 | 1000 | 0.901 | 14.939 | 0.620 | 8.35 | 8.20 |
| | | 0.900 | 14.686 | 0.609 | 8.05 | |
| Example 2-2 | 1200 | 0.901 | 15.278 | 0.628 | 8.65 | 8.69 |
| | | 0.899 | 15.603 | 0.623 | 8.73 | |
| Example 2-3 | 1400 | 0.910 | 14.768 | 0.625 | 8.41 | 8.19 |
| | | 0.900 | 14.793 | 0.598 | 7.96 | |
| Example 2-4 | 1600 | 0.910 | 14.479 | 0.627 | 8.26 | 8.41 |
| | | 0.905 | 14.708 | 0.642 | 8.55 | |
| Example 3-1 | 1000 | 0.909 | 14.225 | 0.613 | 7.93 | 7.93 |
| Example 3-2 | 1200 | 0.910 | 14.885 | 0.639 | 8.65 | 8.55 |
| | | 0.906 | 14.659 | 0.636 | 8.45 | |
| Example 3-3 | 1400 | 0.916 | 14.584 | 0.643 | 8.59 | 8.52 |
| | | 0.906 | 14.511 | 0.641 | 8.44 | |
| Example 3-4 | 1600 | 0.916 | 14.136 | 0.641 | 8.30 | 8.30 |

In Table 1, it can be seen that the organic solar cells in Examples 1-1 to 1-4, 2-1 to 2-4, and 3-1 to 3-4, in which Compound 2 according to an exemplary embodiment of the present specification is used as an electron acceptor, have higher open-circuit voltages, better device efficiencies such as fill factor, and better energy conversion efficiency than those of the organic solar cells in Comparative Examples 1-1 to 1-4, 2-1 to 2-4, and 3-1 to 3-4, in which Comparative Example Compound 1 (IEIC) in the related art is used as an electron acceptor.

$V_{oc}$, $J_{sc}$, FF, and η mean an open-circuit voltage, a short-circuit current, a fill factor, and energy conversion efficiency, respectively. The open-circuit voltage and the short-circuit current are an X axis intercept and an Y axis intercept, respectively, in the fourth quadrant of the voltage-current density curve, and as the two values are increased, the efficiency of the solar cell is desirably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred.

What is claimed is:

1. A heterocyclic compound of Chemical Formula 1:

[Chemical Formula 1]

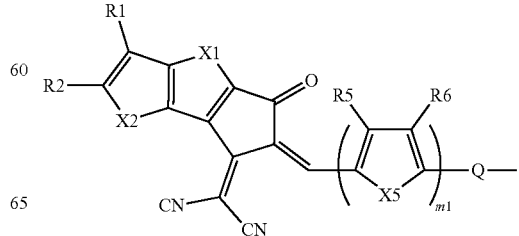

-continued

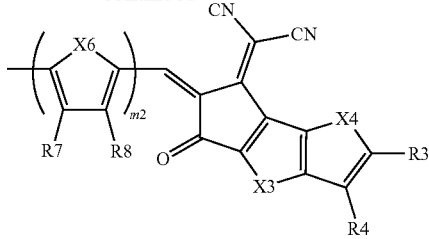

wherein:

X1 to X6 are the same as or different from each other, and are each independently CRR', NR, O, SiRR', PR, S, GeRR', Se, or Te;

R1 to R8, R, and R' are the same as or different from each other, and are each independently hydrogen, deuterium, a halogen group, a hydroxy group, a substituted or unsubstituted alkyl group, or a substituted or unsubstituted alkoxy group;

m1 and m2 are each 0 or 1; and

Q is any one of Chemical Formulae A to C,

[Chemical Formula A]

[Chemical Formula B]

-continued

[Chemical Formula C]

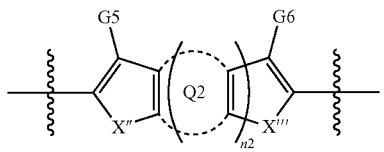

wherein:

X, X', X", and X'" are the same as or different from each other, and are each independently S or Se;

Y1 is CR"R'" or NR";

G1 to G6, R", and R'" are the same as or different from each other, and are each independently hydrogen, deuterium, a halogen group, a hydroxy group, a substituted or unsubstituted alkyl group, a substituted or unsubstituted alkoxy group, a substituted or unsubstituted aryl group, or a substituted or unsubstituted heteroaryl group;

Q1 and Q2 are the same as or different from each other, and are each independently a substituted or unsubstituted ring;

g3 and g4 are each an integer of 1 to 3; and n1 and n2 are each an integer of 1 to 5, wherein two or more structures in the parenthesis are the same as or different from each other.

2. The heterocyclic compound of claim 1, wherein Q1 and Q2 are the same as or different from each other, and are each independently a substituted or unsubstituted aromatic ring, or a substituted or unsubstituted hetero ring.

3. The heterocyclic compound of claim 1, wherein Chemical Formula 1 is any one of Chemical Formulae 1-4 to 1-15:

[Chemical Formula 1-4]

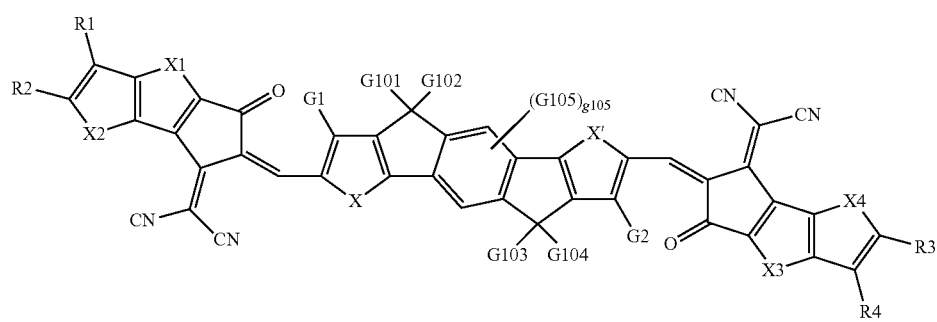

[Chemical Formula 1-5]

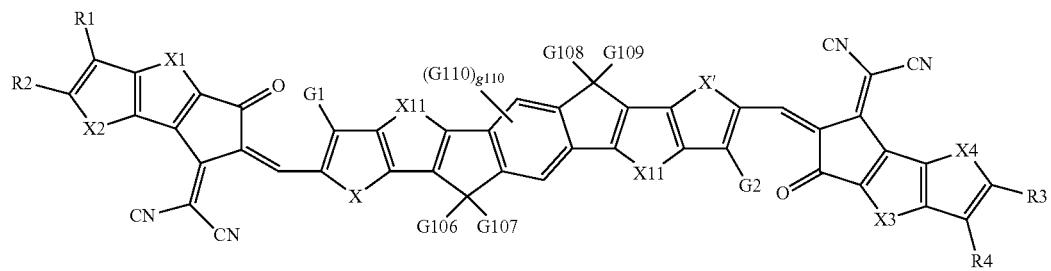

[Chemical Formula 1-6]
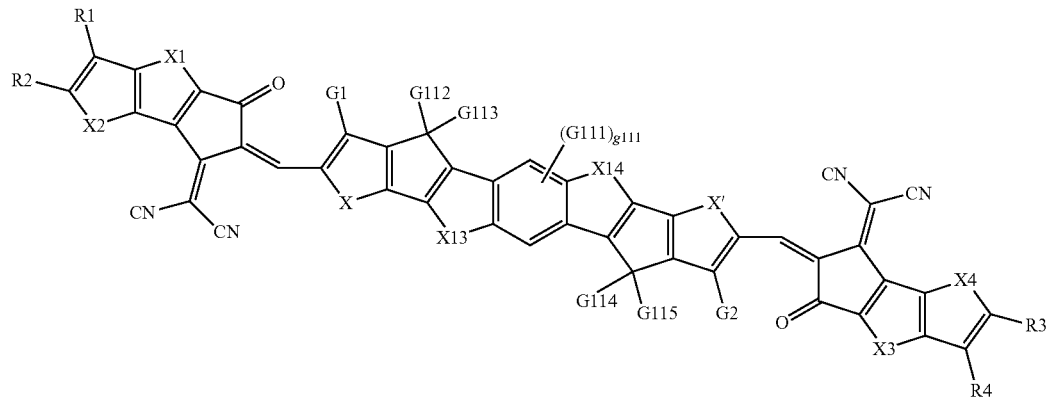
[Chemical Formula 1-7]
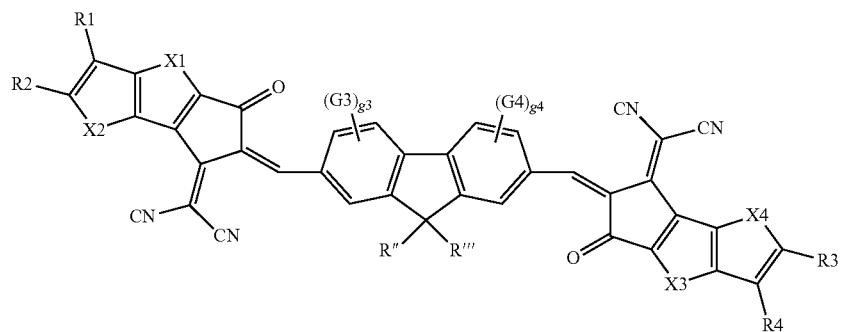
[Chemical Formula 1-8]
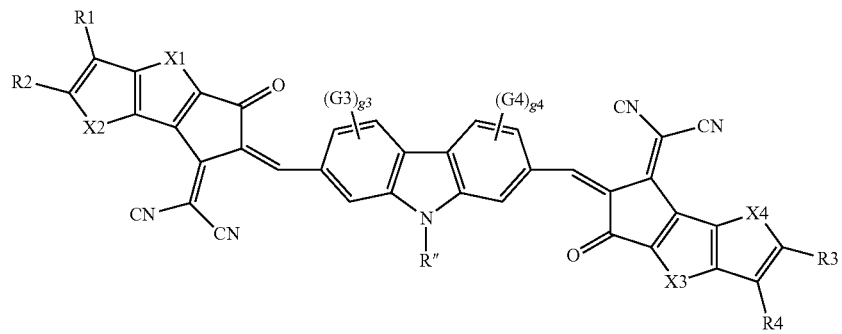
[Chemical Formula 1-9]
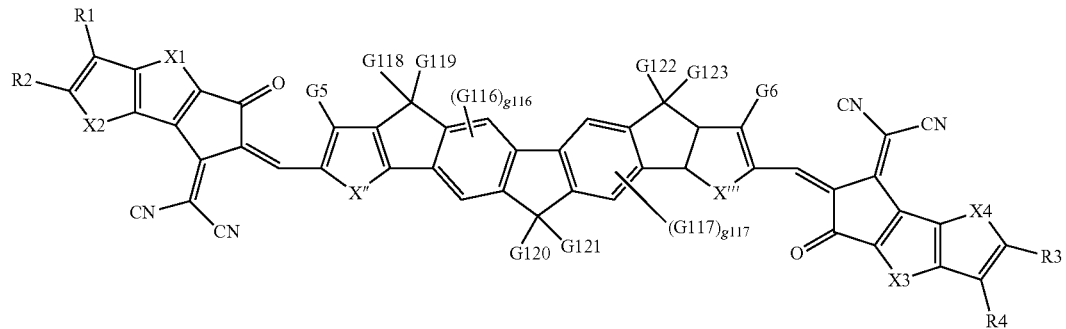

[Chemical Formula 1-10]
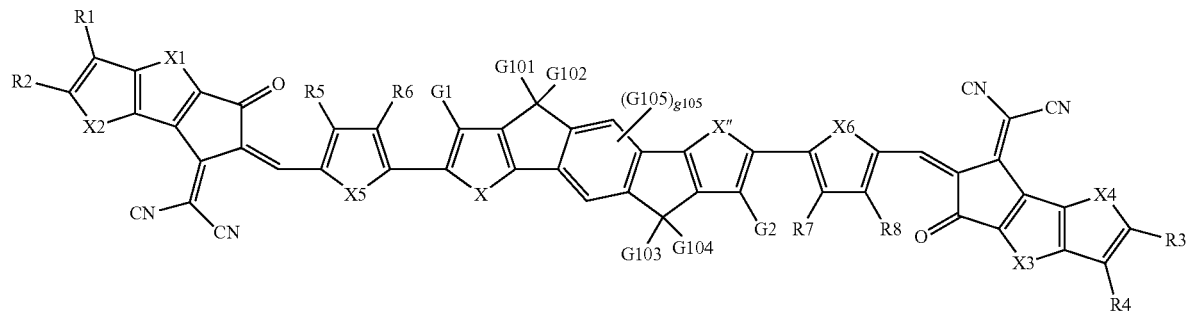
[Chemical Formula 1-11]
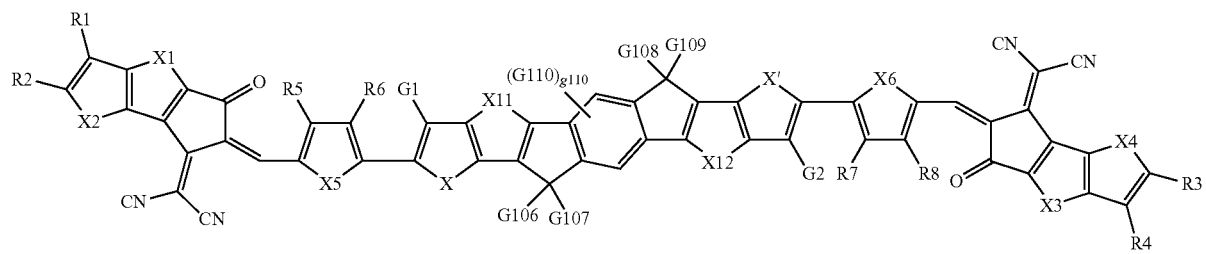
[Chemical Formula 1-12]
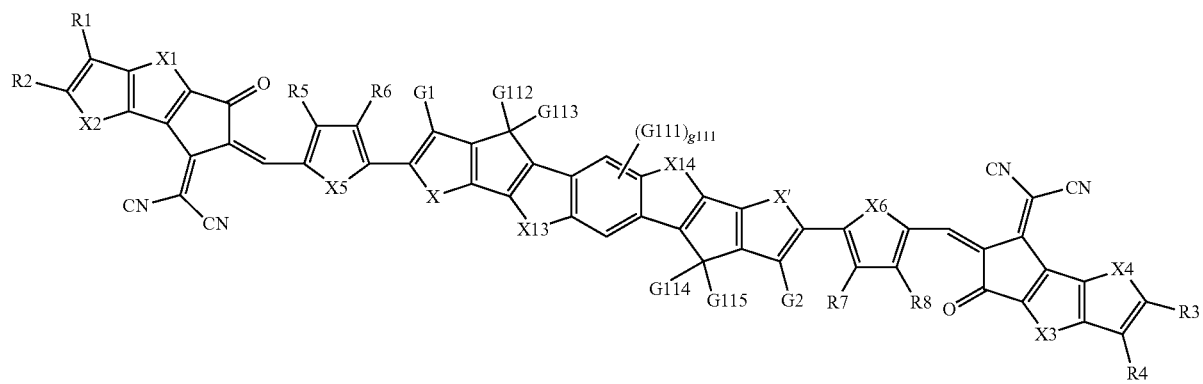
[Chemical Formula 1-13]
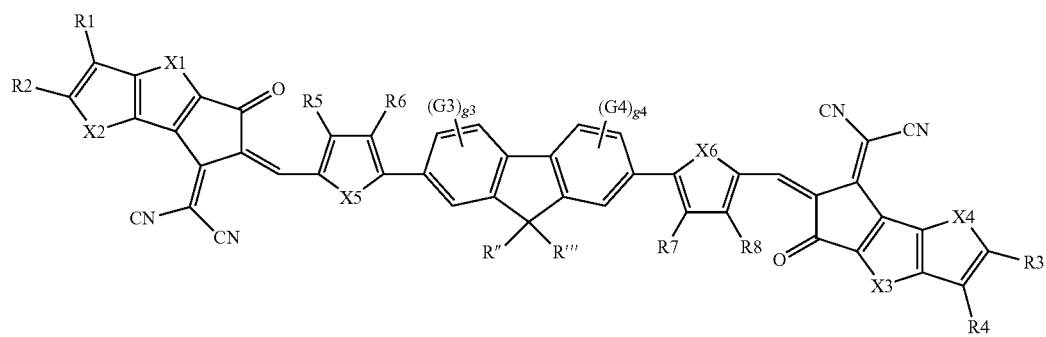

[Chemical Formula 1-14]

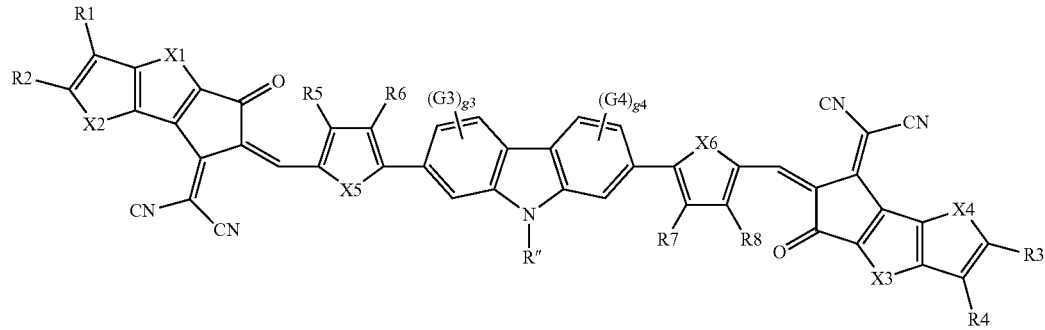

[Chemical Formula 1-15]

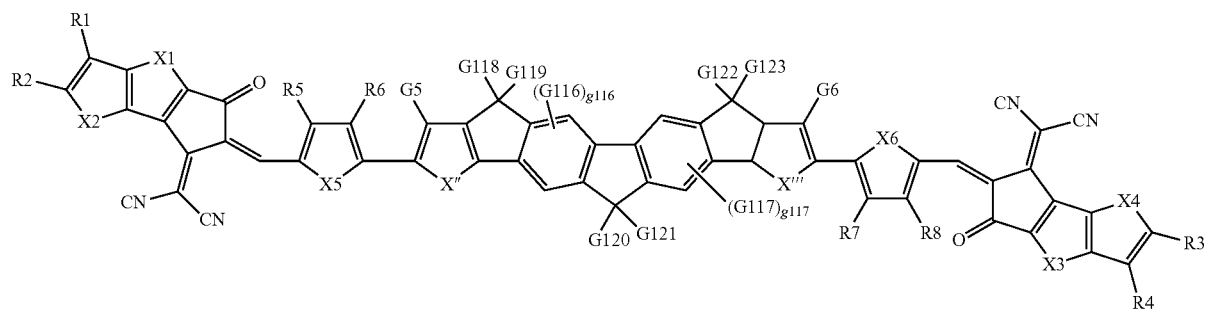

wherein:

X1 to X6, R1 to R8, R, and R' are the same as those defined in Chemical Formula 1;

X, X', G1, and G2 are the same as those defined in Chemical Formula A;

G3, G4, g3, and g4 are the same as those defined in Chemical Formula B;

X", X'", G5, and G6 are the same as those defined in Chemical Formula C;

X11 to X14 are the same as or different from each other, and are each independently S or Se;

G101 to G123, R", and R'" are the same as or different from each other, and are each independently hydrogen, deuterium, a halogen group, a hydroxy group, a substituted or unsubstituted alkyl group, a substituted or unsubstituted alkoxy group, a substituted or unsubstituted aryl group, or a substituted or unsubstituted heteroaryl group; and g105, g110, g111, g116, and g117 are each 1 or 2, and wherein two structures in the parenthesis are the same as or different from each other.

4. The heterocyclic compound of claim 1, wherein Chemical Formula 1 is any one of Chemical Formulae 1-16 to 1-29:

[Chemical Formula 1-16]

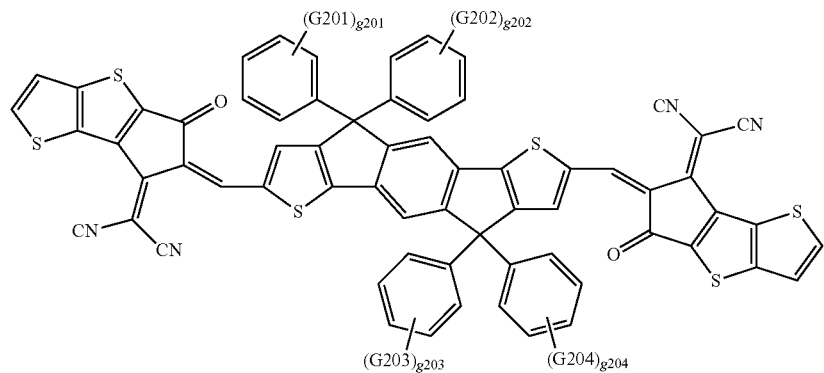

[Chemical Formula 1-17]
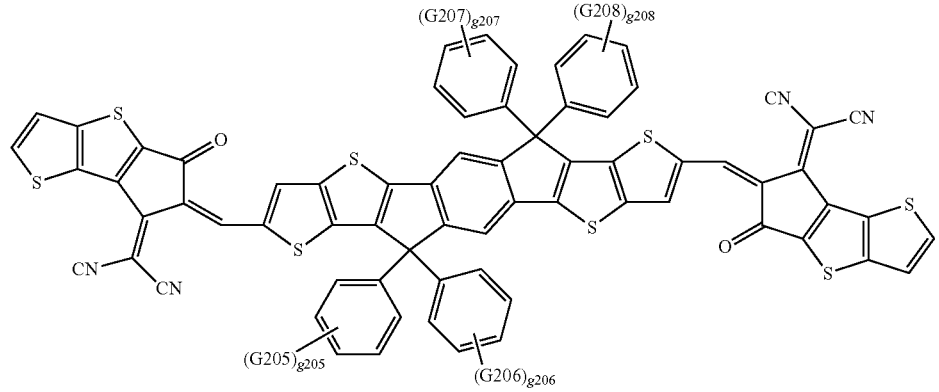
[Chemical Formula 1-18]
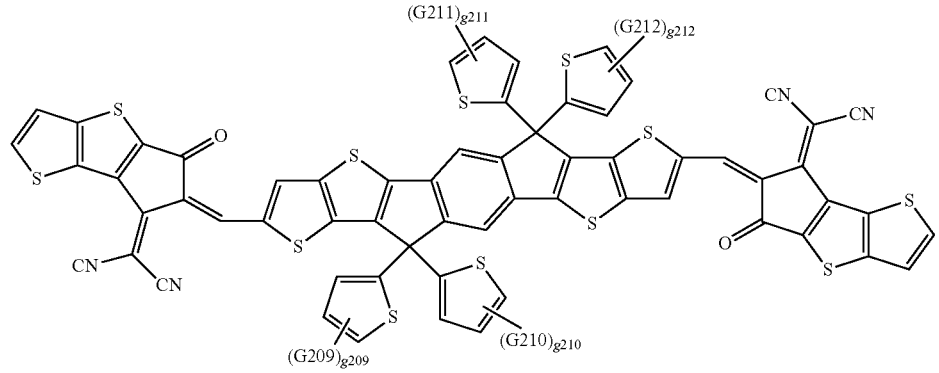
[Chemical Formula 1-19]
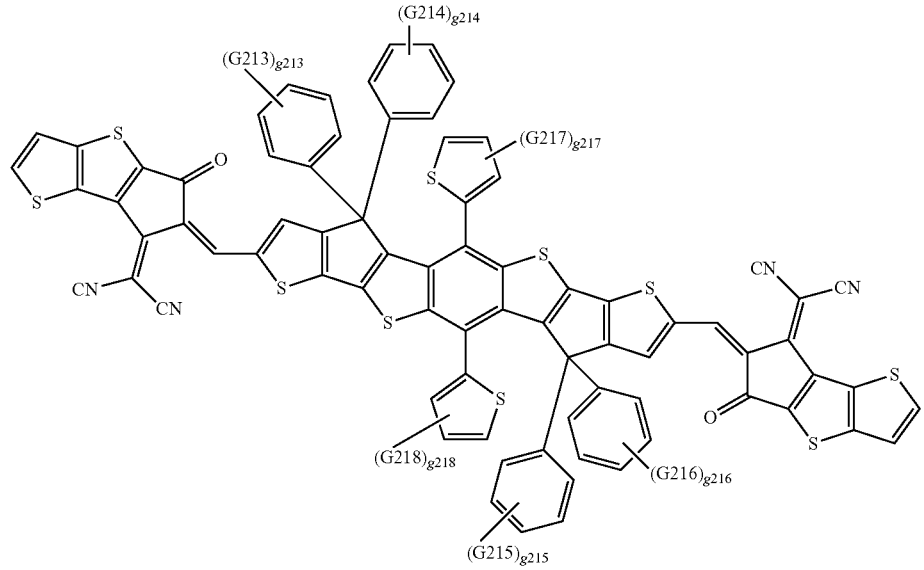
[Chemical Formula 1-20]
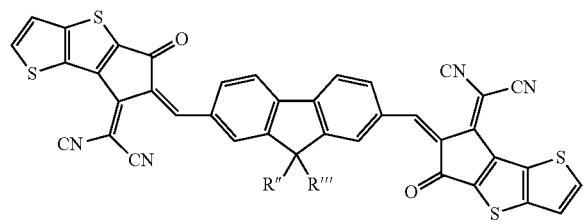
[Chemical Formula 1-21]
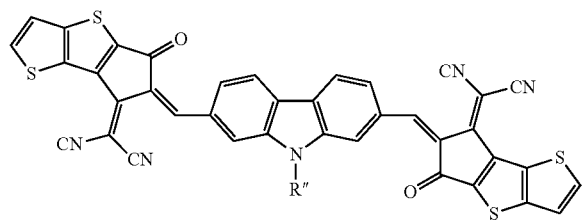

[Chemical Formula 1-22]
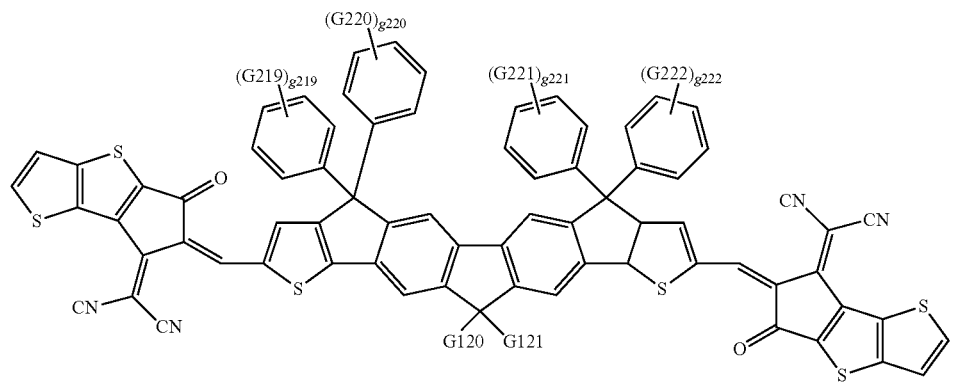
[Chemical Formula 1-23]
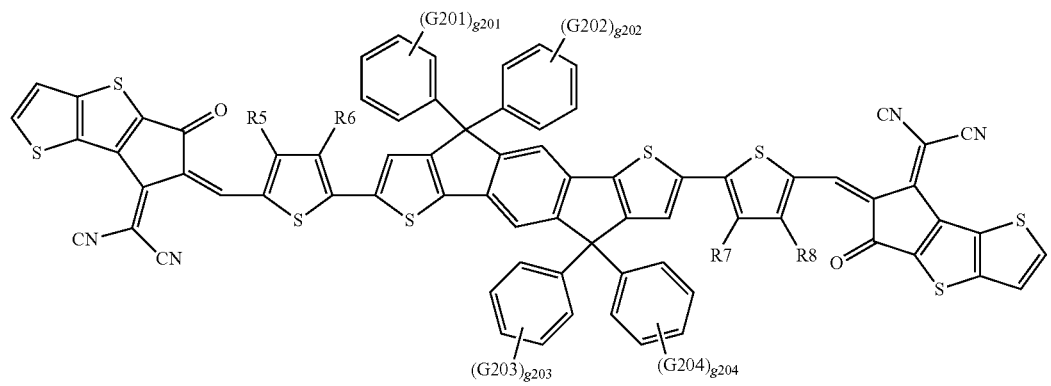
[Chemical Formula 1-24]
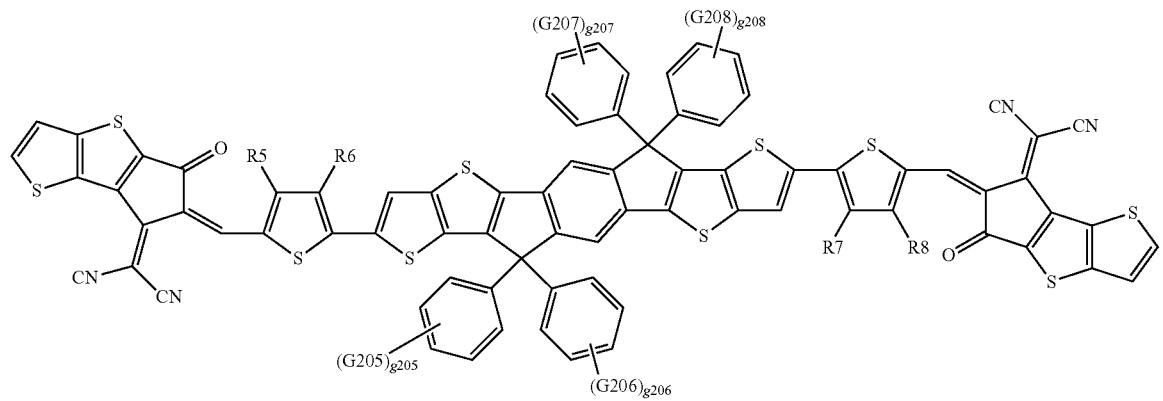
[Chemical Formula 1-25]
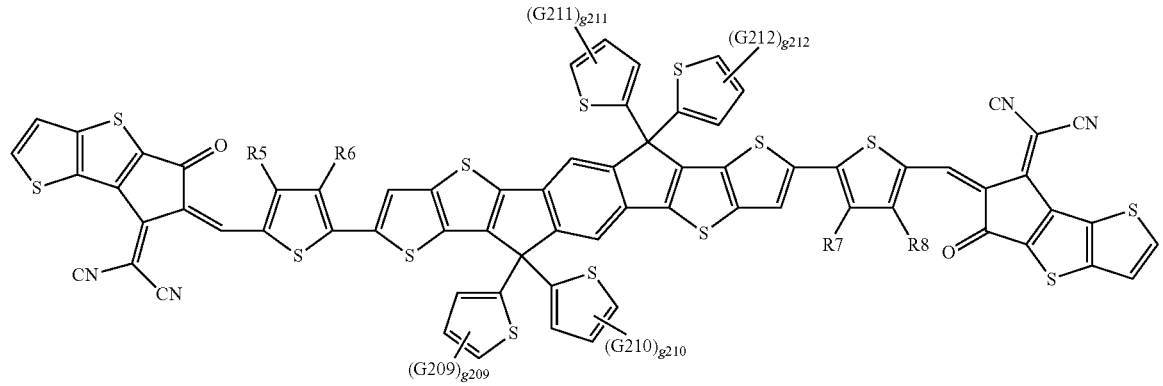

-continued

[Chemical Formula 1-26]

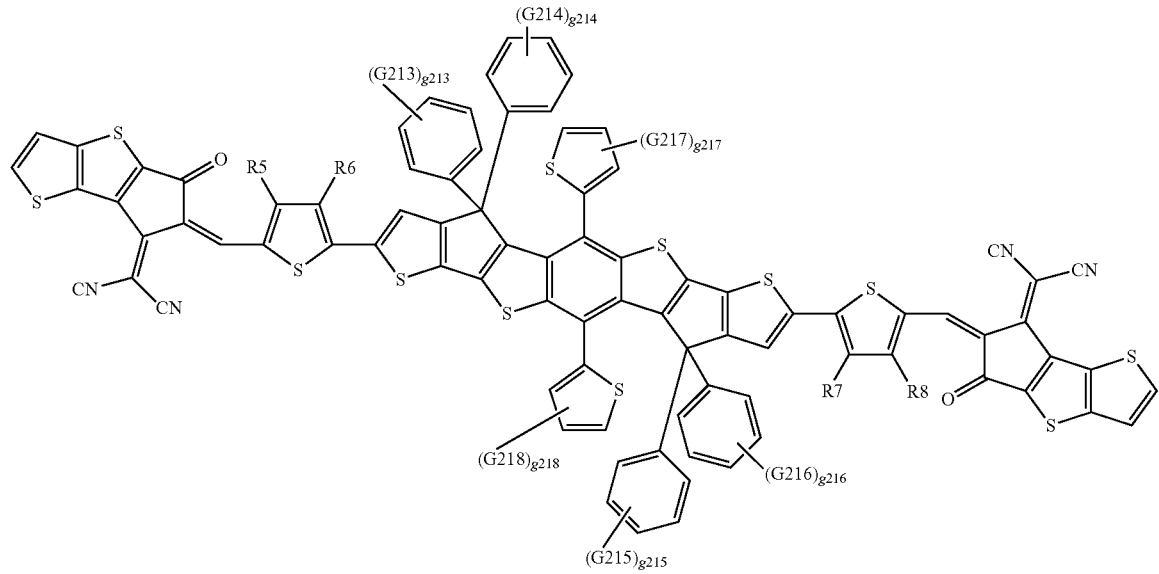

[Chemical Formula 1-27]

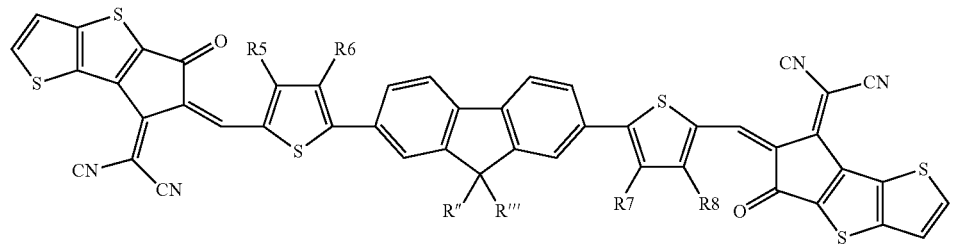

[Chemical Formula 1-28]

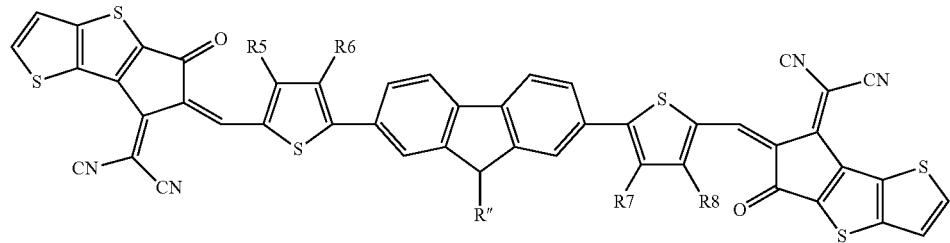

[Chemical Formula 1-29]

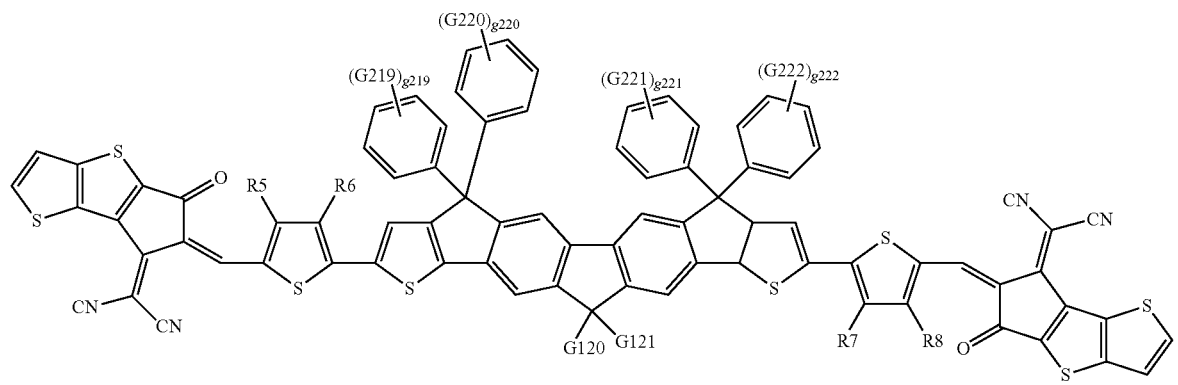

wherein:

R5 to R8 are the same as or different from each other, and are each independently hydrogen, a substituted or unsubstituted alkyl group, or a substituted or unsubstituted alkoxy group;

G120, G121, and G201 to G222 are the same as or different from each other, and are each independently hydrogen, a halogen group, a substituted or unsubstituted alkyl group, or a substituted or unsubstituted thioalkoxy group;

R" and R'" are the same as or different from each other, and are each independently a substituted or unsubstituted alkyl group;

g201 to g208, g213 to g216, and g219 to g222 are each an integer of 1 to 5; and g209 to g212, g217, and g218 are each an integer of 1 to 3, and wherein two or more structures in the parenthesis are the same as or different from each other.

5. The heterocyclic compound of claim 1, wherein Chemical Formula 1 is selected from the following compounds:

[Compound 1]

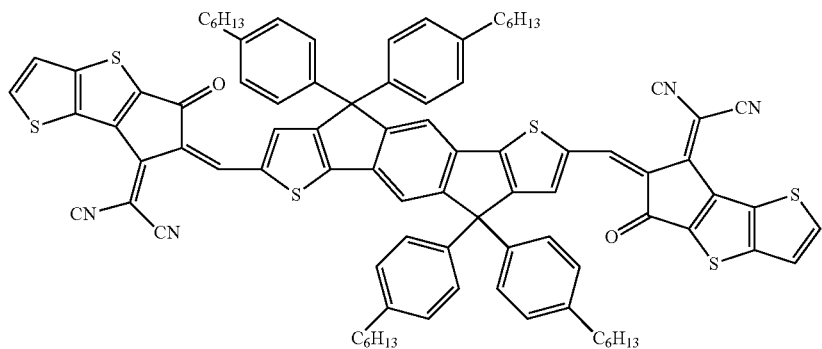

[Compound 2]

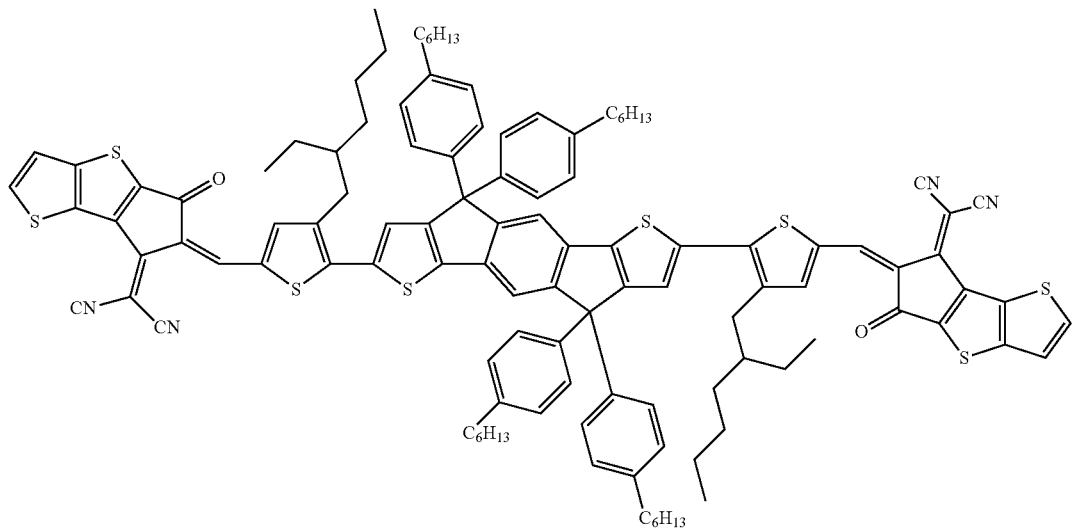

[Compound 3]

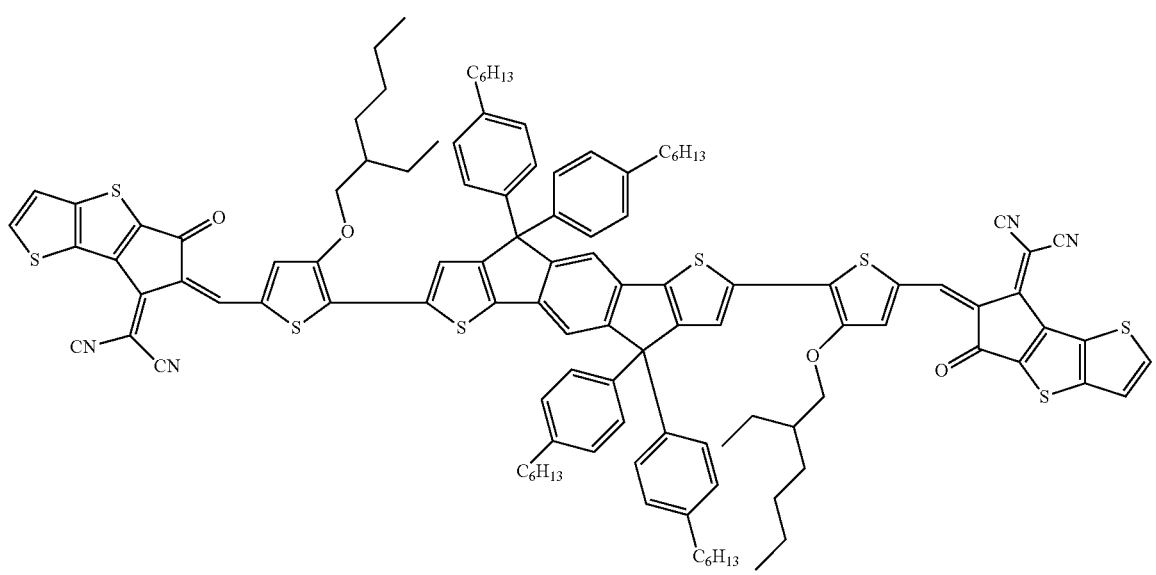

[Compound 4]
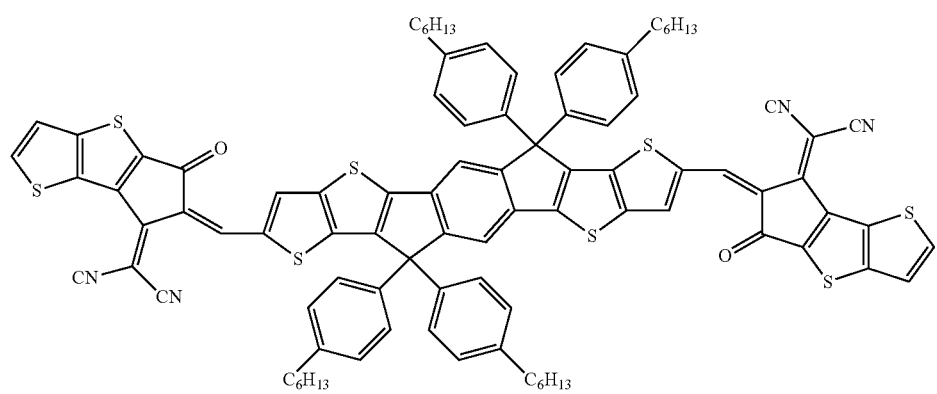
[Compound 5]
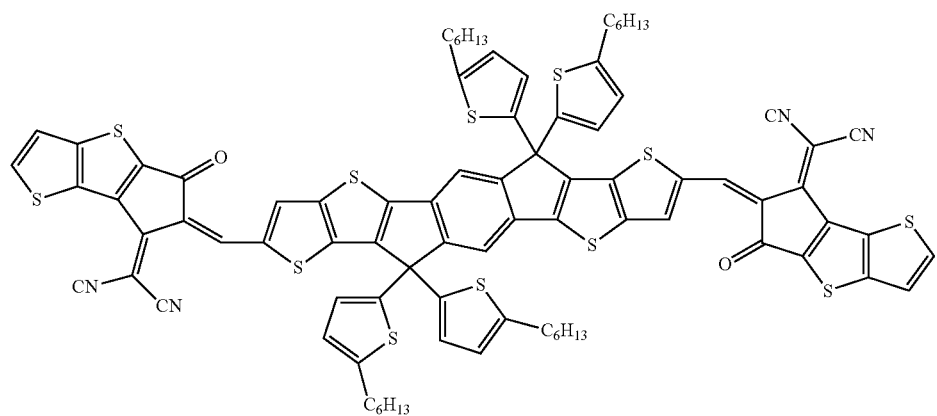
[Compound 6]
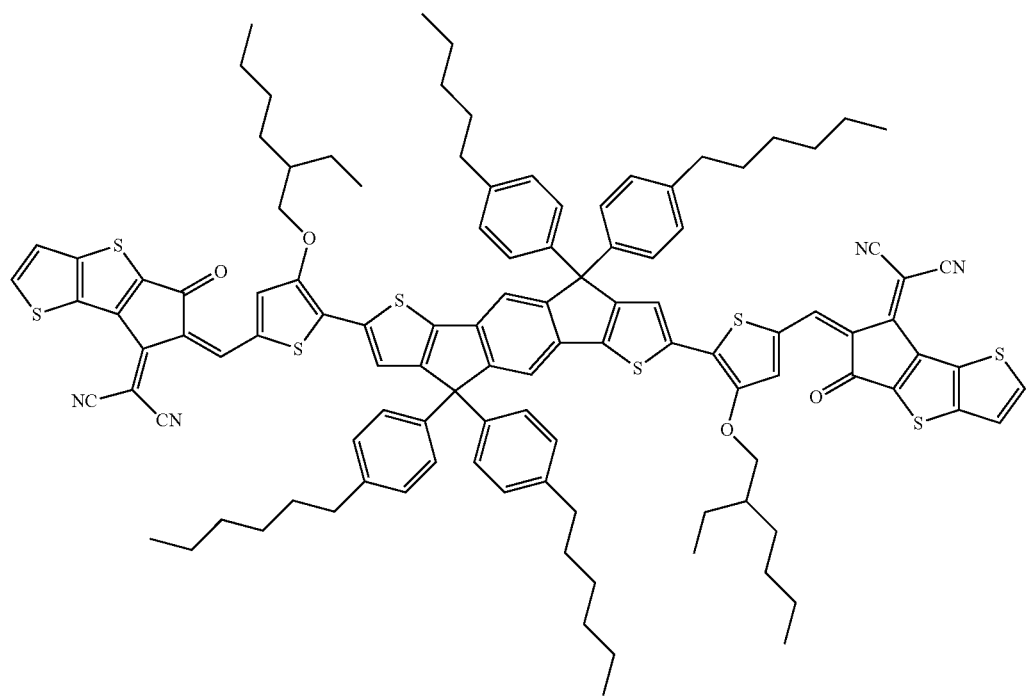

-continued
[Compound 7]
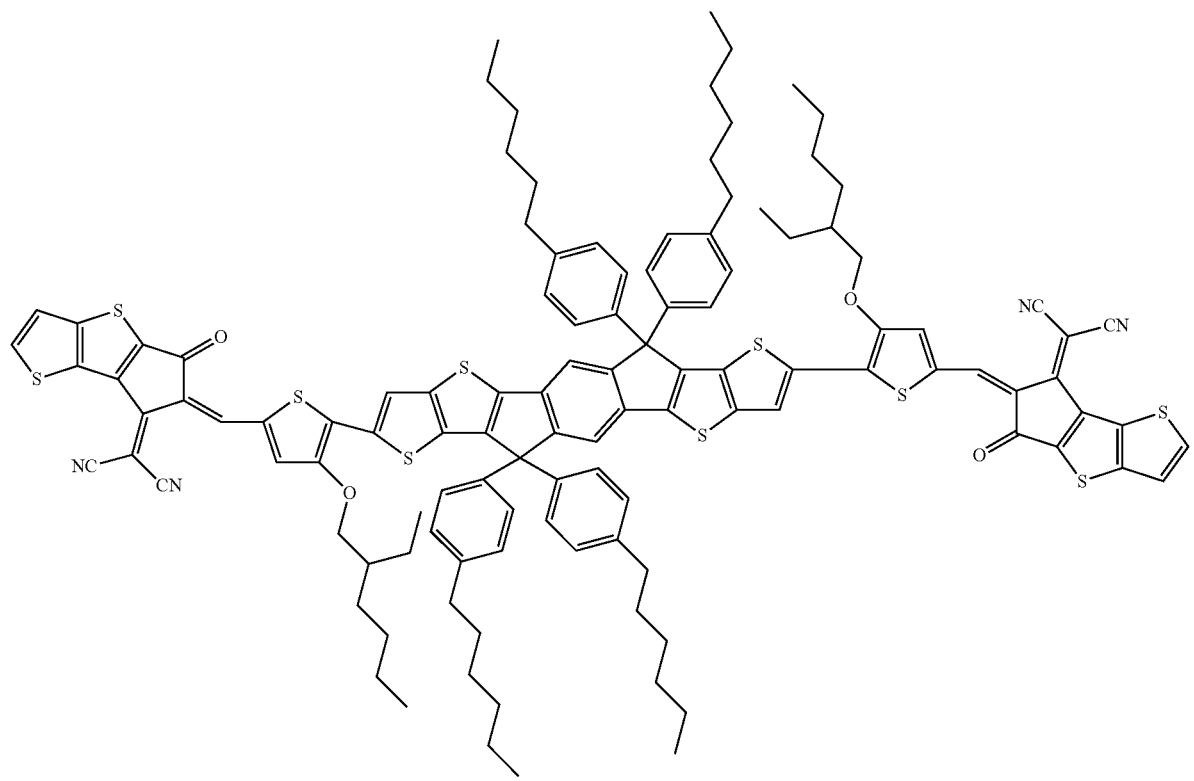
[Compound 8]
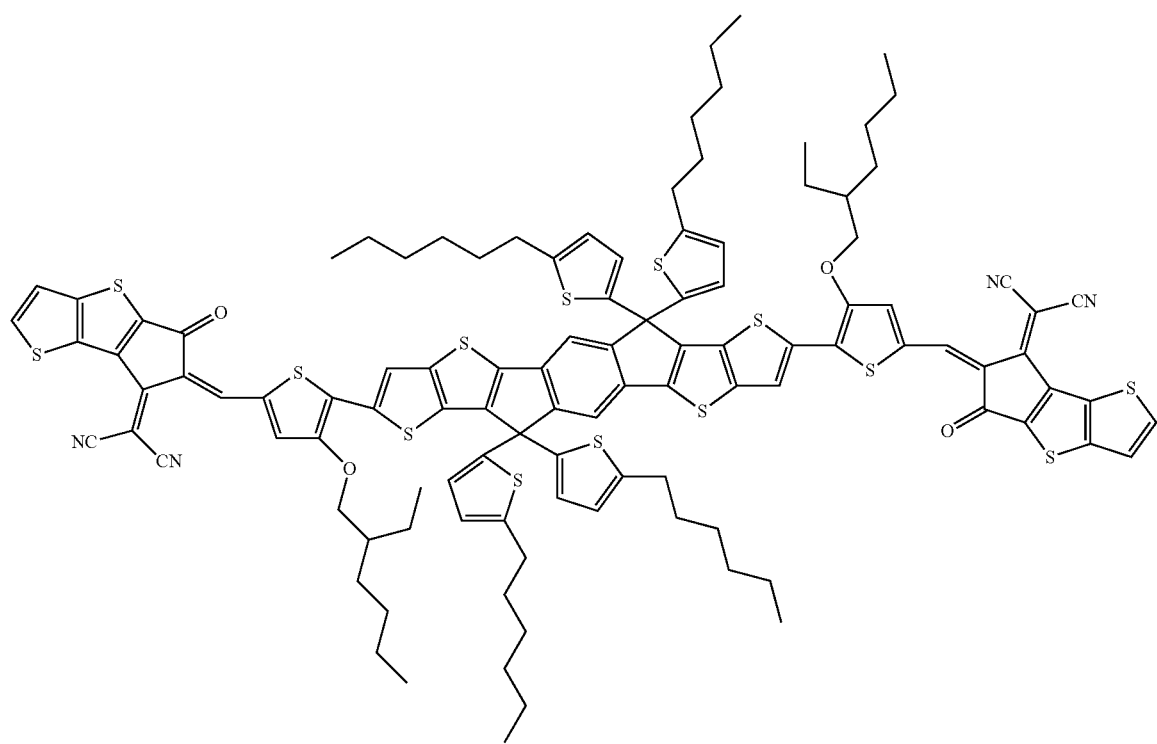

[Compound 9]
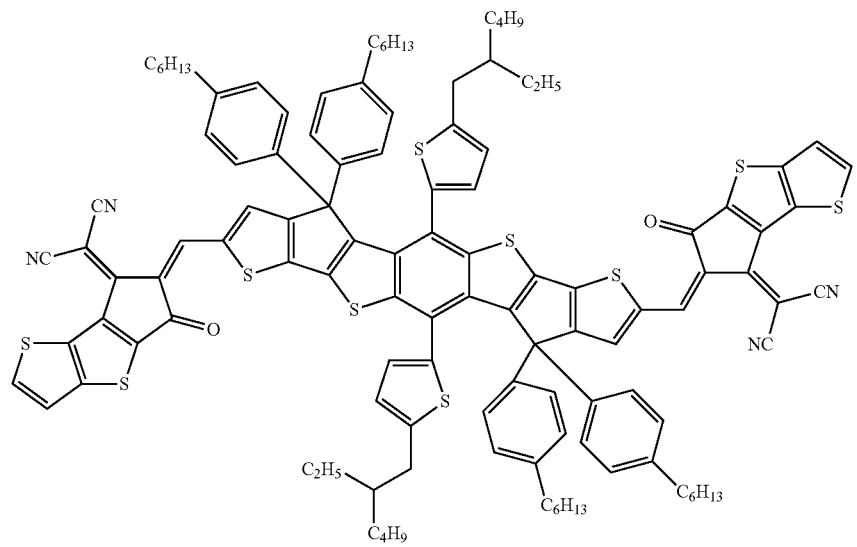
[Compound 10]
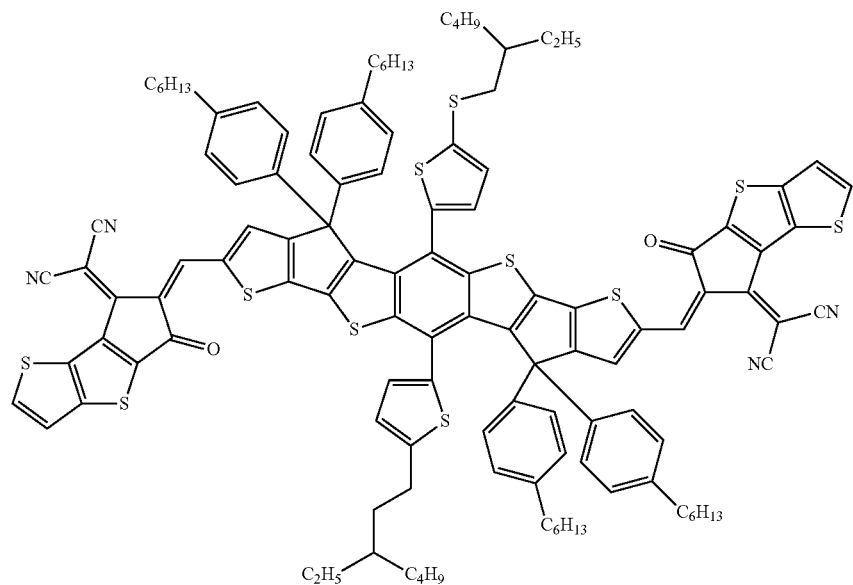
[Compound 11]
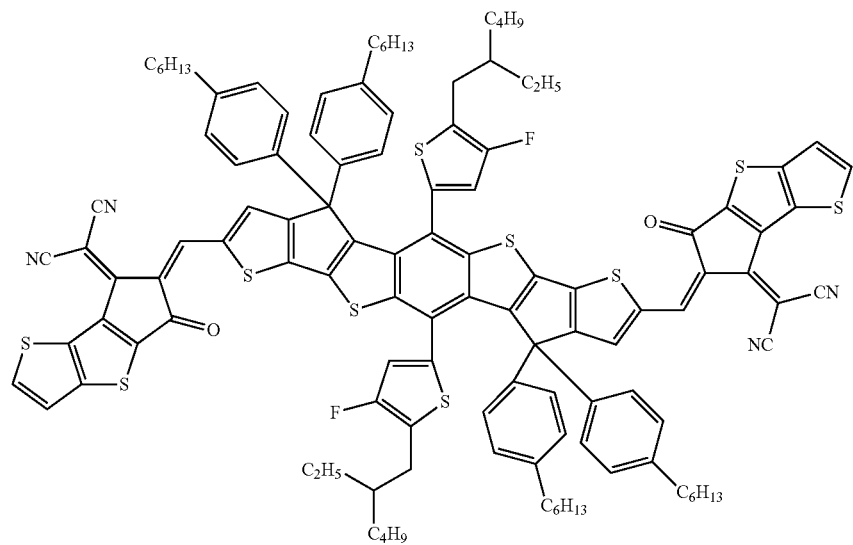

-continued

[Compound 12]

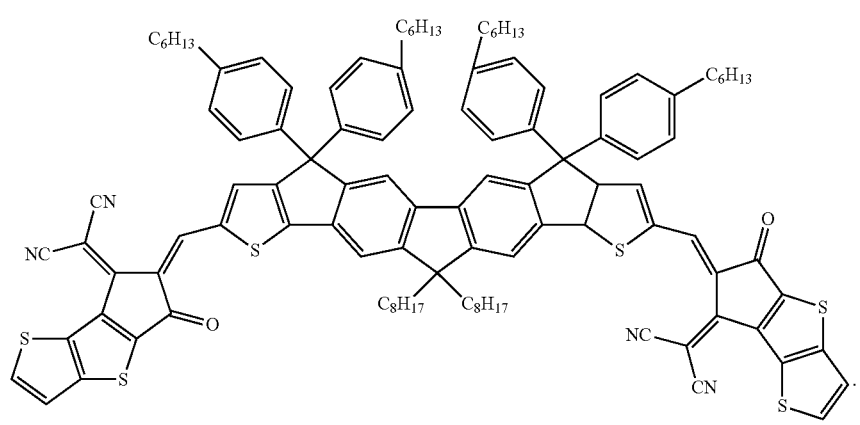

6. An organic electronic device comprising:
a first electrode;
a second electrode facing the first electrode; and
an organic material layer comprising having-one or more layers between the first electrode and the second electrode,
wherein the one or more layers of the organic material layer comprise the heterocyclic compound of claim 1.

7. The organic electronic device of claim 6, wherein the organic material layer comprises a photoactive layer,
wherein the photoactive layer has a bilayer thin film structure comprising an n-type organic material layer and a p-type organic material layer, and wherein the n-type organic material layer comprises the heterocyclic compound of claim 1.

8. The organic electronic device of claim 6, wherein the organic material layer comprises a photoactive layer,
wherein the photoactive layer comprises an electron donor material and an electron acceptor material, and
wherein the electron acceptor material comprises the heterocyclic compound of claim 1.

9. The organic electronic device of claim 8, wherein the electron donor and the electron acceptor constitute a bulk heterojunction (BHJ).

10. The organic electronic device of claim 6, wherein the organic electronic device is selected from the group consisting of an organic photoelectric device, an organic transistor, an organic solar cell, and an organic light emitting device.

11. An organic image sensor comprising the organic electronic device of claim 6.

12. An electronic device comprising the organic image sensor of claim 11.

13. The heterocyclic compound of claim 1, wherein Chemical Formula 1 is Chemical Formula 1-1:

[Chemical Formula 1-1]

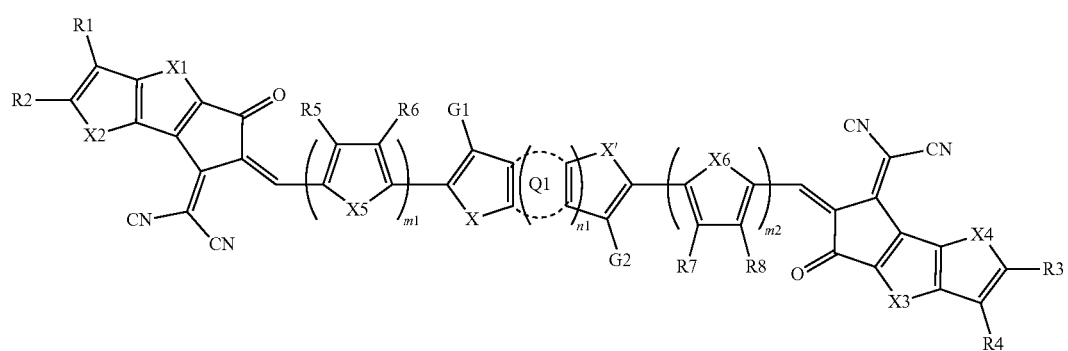

wherein:
X1 to X6, R1 to R8, R, R', m1, and m2 are the same as those defined in Chemical Formula 1; and
Q1, X, X', n1, G1, and G2 are the same as those defined in Chemical Formula A.

14. The heterocyclic compound of claim 1, wherein Chemical Formula 1 is Chemical Formula 1-2:

[Chemical Formula 1-2]

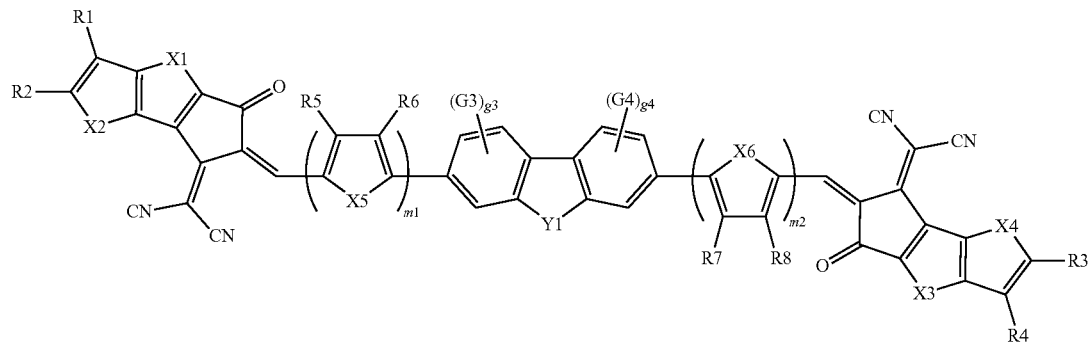

Wherein:
X1 to X6, R1 to R8, R, R', m1, and m2 are the same as those defined in Chemical Formula 1; and
Y1, G3, G4, g3, and g4 are the same as those defined in Chemical Formula B.

15. The heterocyclic compound of claim 1, wherein Chemical Formula 1 is Chemical Formula 1-3:

[Chemical Formula 1-3]

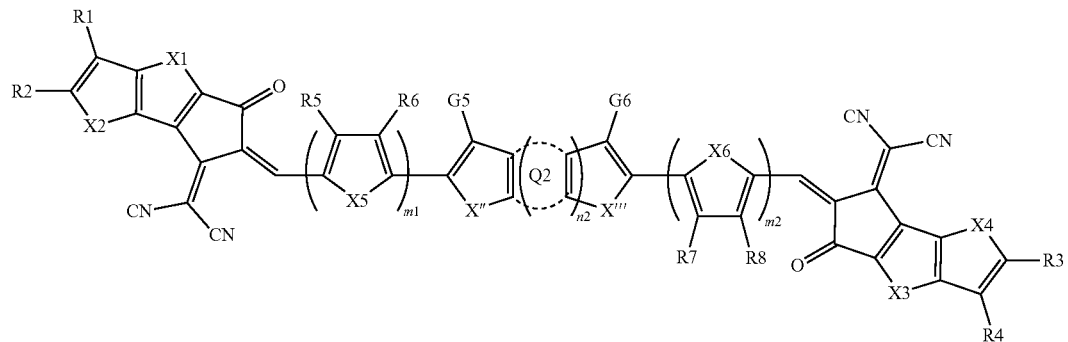

wherein:
X1 to X6, R1 to R8, R, R', m1, and m2 are the same as those defined in Chemical Formula 1; and
Q2, X'', X''', n2, G5, and G6 are the same as those defined in Chemical Formula C.

* * * * *

UNITED STATES PATENT AND TRADEMARK OFFICE
CERTIFICATE OF CORRECTION

PATENT NO. : 11,008,343 B2  
APPLICATION NO. : 16/318277  
DATED : May 18, 2021  
INVENTOR(S) : Kim et al.

Page 1 of 2

It is certified that error appears in the above-identified patent and that said Letters Patent is hereby corrected as shown below:

In the Claims

Column 55, Lines 35-40, Claim 1:  
Please delete Chemical Formula B and replace with the following:

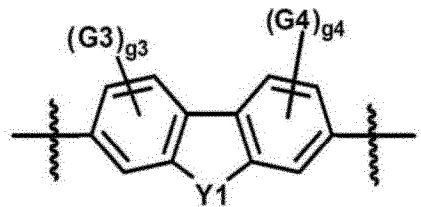

Columns 55-56, Claim 3:  
Please delete Chemical Formula 1-5 and replace with the following:

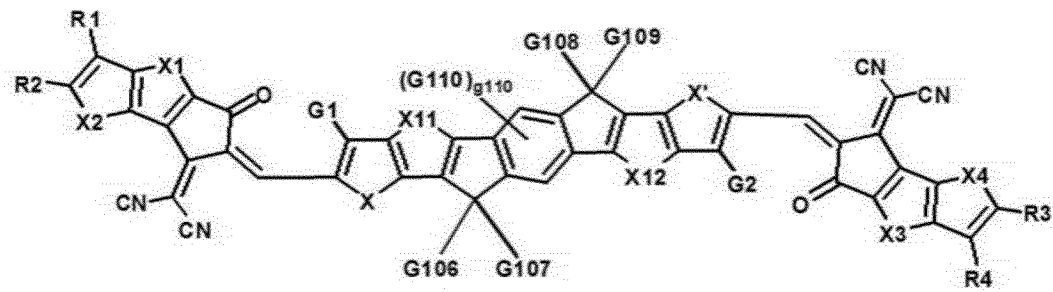

Signed and Sealed this  
Twenty-first Day of September, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 11,008,343 B2

Columns 59-60, Claim 3:
Please delete Chemical Formula 1-10 and replace with the following:

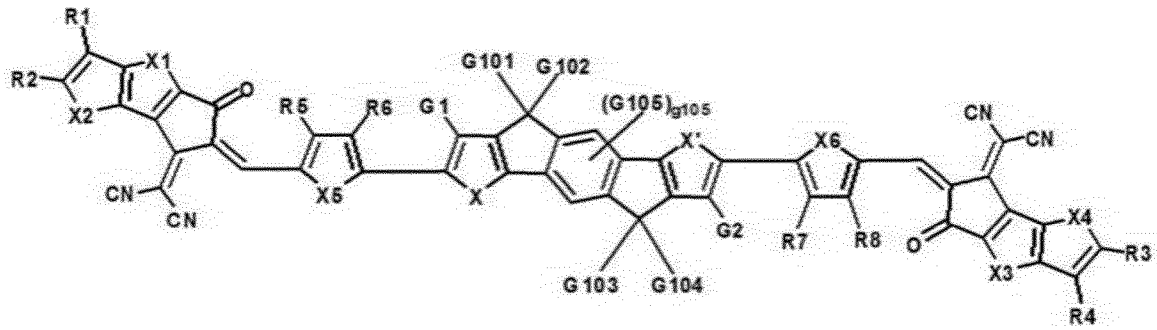

Columns 67-68, Claim 4:
Please delete Chemical Formula 1-28 and replace with the following:

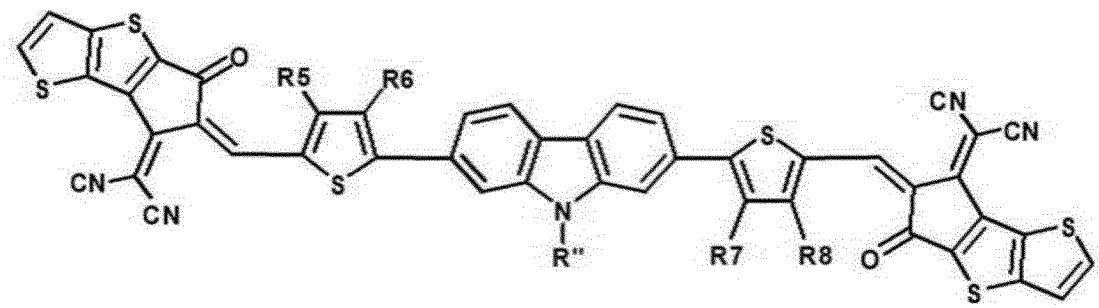

Columns 75-76, Claim 5:
Please delete Compound 10 and replace with the following:

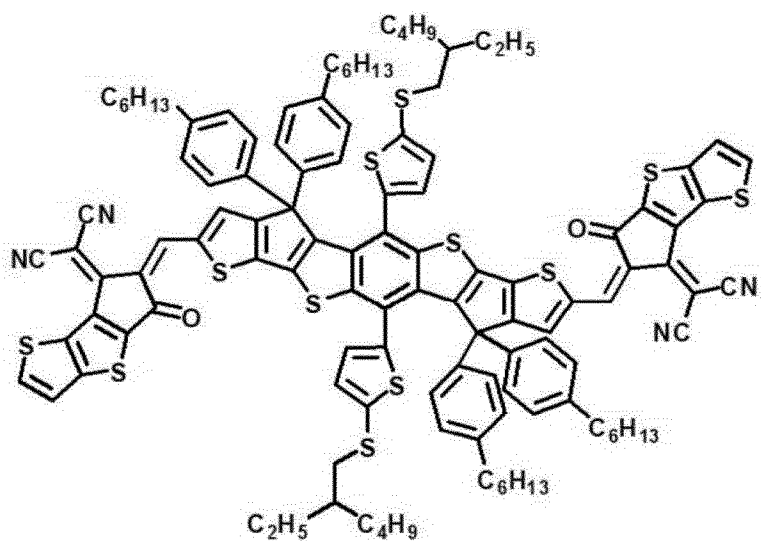

Columns 77, Line 25, Claim 6:
Please correct "comprising having-one" to read -- comprising one --